US008076087B2

(12) United States Patent
Golan et al.

(10) Patent No.: US 8,076,087 B2
(45) Date of Patent: Dec. 13, 2011

(54) GALECTIN SEQUENCES AND COMPOSITIONS AND METHODS UTILIZING SAME FOR TREATING OR DIAGNOSING ARTHRITIS AND OTHER CHRONIC INFLAMMATORY DISEASES

(75) Inventors: Itshak Golan, Tzur-Hadassa (IL); Dan Caspi, Rishon LeZion (IL); Lora Melnik, Beit-Hashmonai (IL)

(73) Assignees: Medical Research Fund of Tel Aviv Sourasky Medical Center, Tel-Aviv (IL); Yissum-Research Development Company of the Hebrew University of Jerusalem, Jerusalem (IL); Yeda Research And Development Co. Ltd., Rehovot (IL)

( * ) Notice: Subject to any disclaimer, the term of this patent is extended or adjusted under 35 U.S.C. 154(b) by 540 days.

(21) Appl. No.: 11/920,054

(22) PCT Filed: May 9, 2006

(86) PCT No.: PCT/IL2006/000548
§ 371 (c)(1),
(2), (4) Date: Feb. 3, 2009

(87) PCT Pub. No.: WO2006/120678
PCT Pub. Date: Nov. 16, 2006

(65) Prior Publication Data
US 2010/0292152 A9    Nov. 18, 2010

Related U.S. Application Data

(63) Continuation of application No. 11/125,263, filed on May 10, 2005, now abandoned, which is a continuation-in-part of application No. PCT/IL03/00960, filed on Nov. 13, 2003, application No. 11/920,054, which is a continuation-in-part of application No. 11/907,893, filed on Oct. 18, 2007, now abandoned.

(60) Provisional application No. 60/428,691, filed on Nov. 25, 2002, provisional application No. 60/426,041, filed on Nov. 14, 2002.

(51) Int. Cl.
*G01N 33/53* (2006.01)
*A61K 39/00* (2006.01)
*A61K 38/04* (2006.01)
*C07K 14/00* (2006.01)

(52) U.S. Cl. ....... 435/7.1; 424/184.1; 530/325; 530/350

(58) Field of Classification Search .................. None
See application file for complete search history.

(56) References Cited

U.S. PATENT DOCUMENTS

| | | |
|---|---|---|
| 3,687,808 A | 8/1972 | Merigan, Jr. et al. |
| 4,036,945 A | 7/1977 | Haber |
| 4,331,647 A | 5/1982 | Goldenberg |
| 4,469,863 A | 9/1984 | Ts'o et al. |
| 4,476,301 A | 10/1984 | Imbach et al. |
| 4,816,567 A | 3/1989 | Cabilly et al. |
| 4,873,316 A | 10/1989 | Meade et al. |
| 4,946,778 A | 8/1990 | Ladner et al. |
| 5,023,243 A | 6/1991 | Tullis |
| 5,034,506 A | 7/1991 | Summerton et al. |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,272,057 A | 12/1993 | Smulson et al. |
| 5,276,019 A | 1/1994 | Cohen et al. |
| 5,278,302 A | 1/1994 | Caruthers et al. |
| 5,286,717 A | 2/1994 | Cohen et al. |
| 5,321,131 A | 6/1994 | Agrawal et al. |
| 5,399,676 A | 3/1995 | Froehler |
| 5,405,938 A | 4/1995 | Summerton et al. |
| 5,405,939 A | 4/1995 | Suhadolnik et al. |
| 5,434,257 A | 7/1995 | Matteucci et al. |
| 5,453,496 A | 9/1995 | Caruthers et al. |
| 5,455,233 A | 10/1995 | Spielvogel et al. |
| 5,464,764 A | 11/1995 | Capecchi et al. |
| 5,466,677 A | 11/1995 | Baxter et al. |
| 5,470,967 A | 11/1995 | Huie et al. |
| 5,476,925 A | 12/1995 | Letsinger et al. |
| 5,487,992 A | 1/1996 | Capecchi et al. |
| 5,489,677 A | 2/1996 | Sanghvi et al. |
| 5,519,126 A | 5/1996 | Hecht |
| 5,536,821 A | 7/1996 | Agrawal et al. |

(Continued)

FOREIGN PATENT DOCUMENTS

EP        0264166        6/1996
(Continued)

OTHER PUBLICATIONS

Official Action Dated Apr. 28, 2010 From the US Patent and Trademark Office Re.: U.S. Appl. No. 11/907,893. Official Action Dated Nov. 6, 2006 From the US Patent and Trademark Office Re.: U.S. Appl. No. 10/505,769.
Official Action Dated Apr. 18, 2007 From the US Patent and Trademark Office Re.: U.S. Appl. No. 10/505,769.
Communication Pursuant to Article 94(3) EPC Dated Dec. 9, 2009 From the European Patent Office Re.: Application No. 03772618.9.
Communication Pursuant to Article 94(3) EPC Dated Nov. 27, 2009 From the European Patent Office Re.: Application No. 03743006.3.

(Continued)

*Primary Examiner* — Maher Haddad

(57) ABSTRACT

Isolated polynucleotides encoding novel galectin-8 variants polypeptides are provided. Also provided are methods and kits using same for diagnosing prognosing and treating rheumatoid arthritis (RA) and other joint/chronic inflammatory diseases.

3 Claims, 16 Drawing Sheets
(11 of 16 Drawing Sheet(s) Filed in Color)

U.S. PATENT DOCUMENTS

| | | | |
|---|---|---|---|
| 5,539,082 | A | 7/1996 | Nielsen et al. |
| 5,541,306 | A | 7/1996 | Agrawal et al. |
| 5,541,307 | A | 7/1996 | Cook et al. |
| 5,545,806 | A | 8/1996 | Lonberg et al. |
| 5,545,807 | A | 8/1996 | Surani et al. |
| 5,550,111 | A | 8/1996 | Suhadolnik et al. |
| 5,561,225 | A | 10/1996 | Maddry et al. |
| 5,563,253 | A | 10/1996 | Agrawal et al. |
| 5,569,825 | A | 10/1996 | Lonberg et al. |
| 5,571,799 | A | 11/1996 | Tkachuk et al. |
| 5,587,361 | A | 12/1996 | Cook et al. |
| 5,596,086 | A | 1/1997 | Matteucci et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,618,704 | A | 4/1997 | Sanghvi et al. |
| 5,623,070 | A | 4/1997 | Cook et al. |
| 5,625,050 | A | 4/1997 | Beaton et al. |
| 5,625,126 | A | 4/1997 | Lonberg et al. |
| 5,633,360 | A | 5/1997 | Bischofberger et al. |
| 5,633,425 | A | 5/1997 | Lonberg et al. |
| 5,661,016 | A | 8/1997 | Lonberg et al. |
| 5,663,312 | A | 9/1997 | Chaturvedula |
| 5,677,437 | A | 10/1997 | Teng et al. |
| 5,677,439 | A | 10/1997 | Weis et al. |
| 5,714,331 | A | 2/1998 | Buchardt et al. |
| 5,719,262 | A | 2/1998 | Buchardt et al. |
| 5,869,289 | A | 2/1999 | Hawkins et al. |
| 5,908,761 | A | 6/1999 | Zick |
| 5,932,447 | A | 8/1999 | Siegall |
| 6,027,916 | A | 2/2000 | Ni et al. |
| 6,281,333 | B1 | 8/2001 | Hawkins et al. |
| 6,303,374 | B1 | 10/2001 | Zhang et al. |
| 6,468,768 | B1 | 10/2002 | Ni et al. |
| 6,759,192 | B1* | 7/2004 | Blumenfeld et al. ............ 435/6 |
| 7,176,181 | B2 | 2/2007 | Zick et al. |
| 2003/0050266 | A1* | 3/2003 | Fisher et al. .................... 514/44 |
| 2005/0215464 | A1 | 9/2005 | Melnik et al. |
| 2006/0009378 | A1 | 1/2006 | Golan et al. |
| 2007/0160602 | A1 | 7/2007 | Zick et al. |
| 2008/0139460 | A1 | 6/2008 | Melnik et al. |

FOREIGN PATENT DOCUMENTS

| | | |
|---|---|---|
| EP | 1767634 | 3/2007 |
| JP | 2003-246749 | 9/2003 |
| WO | WO 95/15175 | 6/1995 |
| WO | WO 98/15624 | 4/1998 |
| WO | WO 99/12041 | 3/1999 |
| WO | WO 99/64590 | 12/1999 |
| WO | WO 02/089831 | 11/2002 |
| WO | WO 03/072606 | 9/2003 |
| WO | WO 2004/043332 | 5/2004 |
| WO | WO 2005/016962 | 2/2005 |
| WO | WO 2006/000548 | 1/2006 |
| WO | WO 2006/120678 | 11/2006 |

OTHER PUBLICATIONS

Communication Pursuant to Article 96(2) EPC Dated Sep. 3, 2007 From the European Patent Office Re.: Application No. 03743006.3.
Office Action Dated Mar. 4, 2010 From the Israel Patent Office Re.: Application No. 187244 and Its Translation Into English.
Office Action Dated Mar. 8, 2010 From the Israeli Patent Office Re.: Application No. 195447 and Its Translation Into English.
Office Action Dated Mar. 8, 2010 From the Israeli Patent Office Re.: Application No. 195448 and Its Translation Into English.
Office Action Dated Jul. 21, 2008 From the Israeli Patent Office Re.: Application No. 168519.
Official Action Dated Jul. 13, 2009 From the US Patent and Trademark Office Re.: U.S. Appl. No. 11/907,893.
Official Action Dated Sep. 17, 2009 From the US Patent and Trademark Office Re.: U.S. Appl. No. 11/907,893.
Official Action Dated Apr. 18, 2007 From the US Patent and Trademark Office Re.: U.S. Appl. No. 10/505,769.
Response Dated Mar. 17, 2010 to Official Action of Sep. 17, 2009 From the US Patent and Trademark Office Re.: U.S. Appl. No. 11/907,893.
Bidon et al. "Galectin-8: A Complex Sub-Family of Galectins (Review)", International Journal of Molecular Medicine, 8(3): 245-250, 2001. Abstract.
Germain et al. "Cleavage of Automodified Poly(ADP-Ribose) Polymerase During Apoptsis", Journal of Biological Chemistry, 274(40): 28379-28384, 1999.
Gopalkrishnan et al. "Molecular Characterization of Prostate Carcinoma Tumor Antigen-1, PCTA-1, A Human Galectin-8 Related Gene", Oncogene, 19: 4405-4416, 2000. Abstract.
Hadari et al. "Galectin-8 Binding to Integrins Inhibits Cell Adhesion and Induces Apoptosis", Journal of Cell Science, XP002250560, 113(13): 2385-2397, 2000. Abstract. p. 2391, col. 2.
Hadari et al. "Galectin-8: On the Road From Structure to Function", Trends in Glycoscience and Glycotechnology, 9(45): 103-112, 1997.
Katoh et al. "Galectin-9 Inhibits CD44-Hyaluronan Interaction and Suppresses a Murine Model of Allergic Asthma", American Journal of Respiratory and Critical Medicine, 176(1): 27-35, Jul. 1, 2007.
Lazebnik "Cleavage of Poly(ADP-Ribose) Polymerase by a Proteinase With Properties Like ICE", Nature, 371(6495): 346-347, 1994. Abstract.
Lesley et al. "CD44 and Its Interaction With Extracellular Matrix", Advances in Immunology, 54: 271-335, 1993. Abstract.
Lesley et al. "Variant Cell Lines Selected for Alterations in the Function of the Hyaluronan Receptor CD44 Show Differences in Glycosylation", Journal of Experimental Medicine, 182: 431-437, 1995.
Levy et al. "Galectin-8 Functions as a Matricellular Modulator of Cell Adhesion", The Journal of Biological Chemistry, 276(33): 31285-31295, 2001.
Lio "Galectins: A New Family of Regulators of Inglammation", Clinical Immunology, 97: 79-88, 2000.
Naor et al. "CD44: Structure, Function, and Asssociation With the Malignant Process", Advances in Cancer Research, 71: 241-319, 1997. Abstract.
Screaton et al. "The Identification of a New Alternative Exon With Highly Restricted Tissue Expression in Transcripts Encoding the Mouse Pgp-1 (CD44) Homing Receptor", The Journal of Biological Chemistry, 268(17): 12235-12238, 1993.
Van Weering et al. "A PCR-Based Method for the Analysis of Human CD44 Splice Products", PCR Methods and Applications, 3: 100-106, 1993.
Ward et al. "Blocking Adhesion Molecules in Vivo as Anti-Inflammatory Therapy", Therapeutic Immunology, 1(3): 165-171, 1994.
Yifat et al. "Galectin-8 Functions as a Matricellular Modulator of Cell Adhesion", The Journal of Biological Chemistry, 276 (33): 31285-31295, 2001.
Response Dated Jun. 7, 2010 to Communication Pursuant to Article 94(3) EPC of Dec. 9, 2009 From the European Patent Office Re.: Application No. 03772618.9.
Office Action Dated Mar. 7, 2010 From the Israel Patent Office Re. Application No. 195446.
Response Dated Jul. 6, 2010 to Office Action of Mar. 7, 2010 From the Israel Patent Office Re. Application No. 195446.
Response Dated Aug. 4, 2010 to Office Action of Mar. 4, 2010 From the Israel Patent Office Re.: Application No. 187244.
Barondes et al. "Galectins. Structure and Function of a Large Family of Animal Lectins", The Journal of Biological Chemistry, 269(33): 20807-20810, 1994.
Bresalier et al. "Colon Cancer Mucin: A New Ligand for the β-Galactoside-Binding Protein Galectin-3", Cancer Research, 56: 4354-4357, 1996.
Cherayil et al. "Molecular Cloning of a Human Macrophage Lectin Soecific for Galactose", Proc. Natl. Acad. Sci. USA, 87: 7324-7328, 1990.
Dagher et al. "Identification of Galectin-3 as a Factor in Pre-mRNA Splicing", Proc. Natl. Acad. Sci. USA, 92: 1213-1217, 1995.
Drickamer et al. "Biology of Animal Lectins", Annual Reviews in Cell Biology, 9: 237-264, 1993.
Gitt et al. "Galactin-4 and Galactin-6 Are Two Closely Related Lectins Expressed in Mouse Gastrointestinal Tract", The Journal of Biological Chemistry, 273(5): 2954-2960, 1998.
Haagsma et al. "Combination of Sulphasalazine and Methotrexate Versus the Single Components in Early Rheumatoid Arthritis: A Randomized, Controlled, Double-Blind, 52 Week Clinical Trial", British Journal of Rheumatology, 36(10): 1082-1088, 1997. Claims: 1-20, 22-32, 34-35, 38.

Hadari et al. "Galectin-8 Binding to Integrins Inhibits Cell Adhesion and Induces Apoptosis", J. of Cell Science, 113(Pt.13): 2385-2397, 2000. Claims: 1-20, 22-32, 34-35, 38.

Hadari et al. "Galectin-8. A New Rat Lectin, Related to Galectin-4", The Journal of Biological Chemistry, 270(7): 3447-3453, 1995.

Ilarregui et al. "The Coming of Age of Galectins as Immunomodulatory Agents: Impact of These Carbohydrate Binding Proteins in T Cell Physiology and Chronic Inflammatory Disorders", Annals of the Rheumatic Diseases, 64: iv96-iv103, 2005.

Jia et al. "Carbohydrate Binding Protein 35. Complementary DNA Sequence Reveals Homology With Proteins of the Heterogeneous Nuclear RNP", The Journal of Biological Chemistry, 263(13): 6009-6011, 1988.

Leonidas et al. "Structural Basis for the Recognition of Carbohydrates by Human Galectin-7", Biochemistry, 37: 13930-13940, 1998.

Levy et al. "Galectin-8 Functions as a Matricellular Modulator of Cell Adhesion", The Journal of Biological Chemistry, 276(33): 31285-31295, 2001.

Levy et al. "It Depends on the Hinge: A Structure-Functional Analysis of Galectin-8, A Tandem-Repeat Type Lectin", Glycobiology, 16(6): 463-476, 2006.

Liu et al. "S-Type Mammalian Lectins in Allergic Inflammation", Immunology Today, 14(10): 486-490, 1993.

McEver et al. "Leukocyte Trafficking Mediated by Selectin-Carbohydrate Interactions", The Journal of Biological Chemistry, 270(19): 11025-11028, 1995.

Schoeppner et al. "Expression of an Endogenous Galactose-Binding Lectin Correlates With Neoplastic Progression in the Colon", Cancer, 75: 2818-2826, 1995.

Su et al. "Surface-Epitope Masking and Expression Cloning Identifies the Human Prostate Carcinoma Tumor Antigen Gene PCTA-1 A Member of the Galectin Gene Family", Proc. Natl. Acad. Sci. USA, 93(14): 7252-7257, 1996. Claims: 1-20, 22-32, 34-35, 38.

Vyakarnam et al. "Evidence for A Role for Galectin-1 in Pre-mRNA Splicing", Molecular and Cellular Biology, 17(8): 4730-4737, 1997.

Wada et al. "Identification and Characterization of Galactin-9, A Novel β-Galactoside-Binding Mammalian Lectin", The Journal of Biological Chemistry, 272(9): 6078-6086, 1997.

Yang et al. "Expression of Galectin-3 Modulates T-Cell Growth and Apoptosis", Proc. Natl. Acad. Sci. USA, 93: 6737-6742, 1996.

Requisition by the Examiner Dated Jul. 16, 2010 From the Canadian Intellectual Property Office Re. Application No. 2,505,931.

Examiner's Report Dated Apr. 7, 2008 From the Australian Government, IP Australia Re.: Application No. 2005201964.

International Preliminary Report on Patentability Dated Jan. 22, 2009 From the International Bureau of WIPO Re.: Application No. PCT/IL2006/000548.

International Search Report Dated Jul. 29, 2008 From the International Searching Authority by the Patent Cooperation Treaty Re.: application PCT/IL06/00548.

Office Action Dated May 7, 2009 From the Israeli Patent Office Re.: Application No. 168519 and Its Translation Into English.

Office Action Dated May 10, 2009 From the Israeli Patent Office Re.: Application No. 195446 and Its Translation Into English.

Office Action Dated May 10, 2009 From the Israeli Patent Office Re.: Application No. 195447 and Its Translation Into English.

Office Action Dated May 10, 2009 From the Israeli Patent Office Re.: Application No. 195448 and Its Translation Into English.

Official Action Dated Oct. 13, 2006 From the US Patent and Trademark Office Re.: U.S. Appl. No. 11/125,263.

Official Action Dated Apr. 17, 2007 From the US Patent and Trademark Office Re.: U.S. Appl. No. 11/125,263.

Supplementary European Search Report Dated Jul. 10, 2009 From the European Patent Office Re.: Application No. 03772618.9.

Written Opinion Dated Jul. 29, 2008 From the International Searching Authority by the Patent Cooperation Treaty Re.: Application PCT/IL06/00548.

Bidon et al. "Galectin-8: A Complex Sub-Family of Galectins (Review)", International Journal of Molecular Medicine, XP008107660, 8(3): 245-250, Sep. 2001.

Lahm et al. "Comprehensive Galectin Fingerprinting in a Panel of 61 Human Tumor Cell Lines by RT-PCR and Its Implications for Diagnostic and Therapeutic Procedures", Journal of Cancer Research and Clinical Oncology, XP002534530, 127(6): 375-386, 2001. Abstract.

Naor et al. "CD44 Involvement in Autoimmune Inflammations: The Lesson to Be Learned From CD44-Targeting by Antobody or From Knockout Mice", Annals of the New York Academy of Sciences, 1110: 233-247, 2007.

Sebban et al. "The Involvement of CD44 and Its Novel Ligand Galectin-8 in Apoptotic Regulation of Autoimmune Inflammation", The Journal of Immunology, 179: 1225-1235, 2007.

Response Dated Jan. 6, 2011 to Requisition by the Examiner of Jul. 16, 2010 From the Canadian Intellectual Property Office Re. Application No. 2,505,931.

Communication Pursuant to Article 94(3) EPC Dated Oct. 25, 2010 From the European Patent Office Re.: Application No. 03772618.9.

Response Dated Mar. 8, 2011 to Official Action of Dec. 9, 2010 From the US Patent and Trademark Office Re.: U.S. Appl. No. 11/920,054.

Response Dated Feb. 16, 2011 to Communication Pursuant to Article 94(3) EPC of Oct. 25, 2010 From the European Patent Office Re.: Application No. 03772618.9.

\* cited by examiner

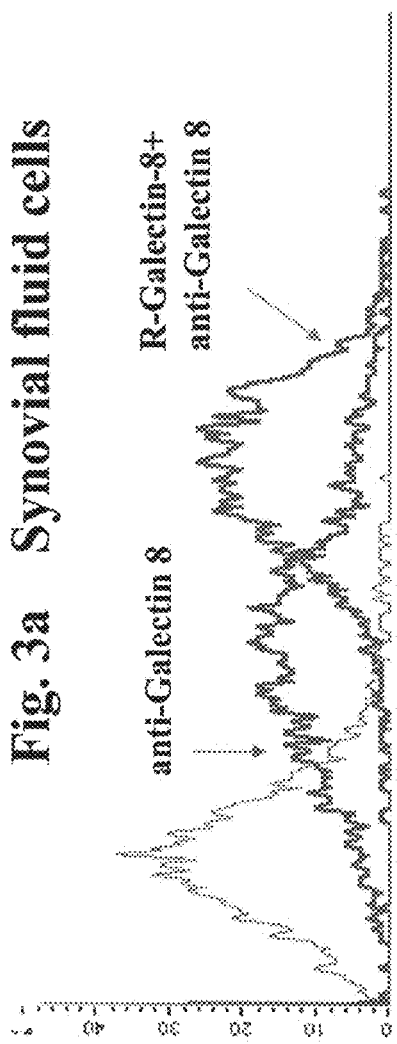
Fig. 3a Synovial fluid cells
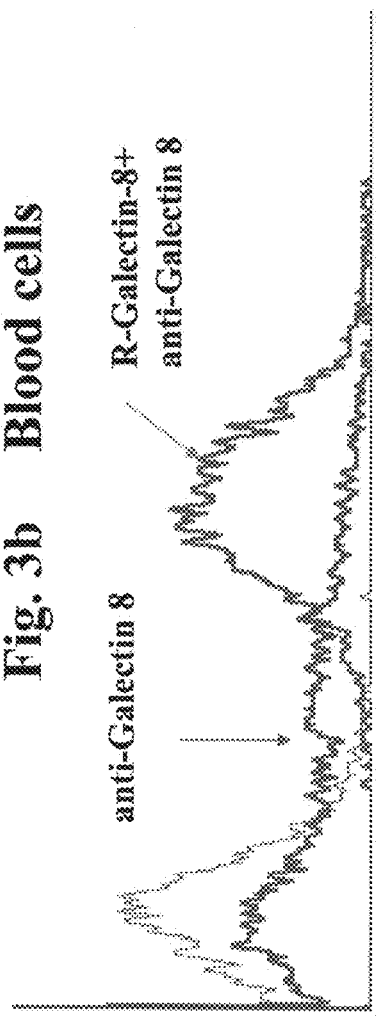
Fig. 3b Blood cells

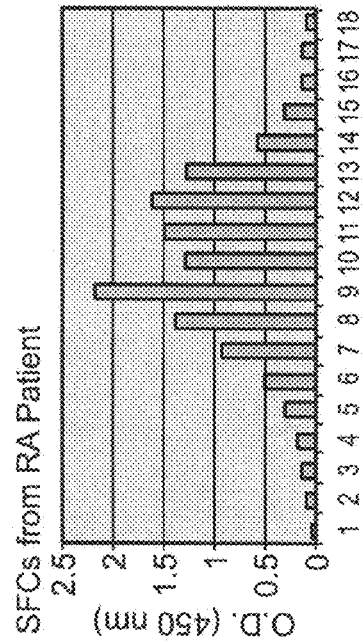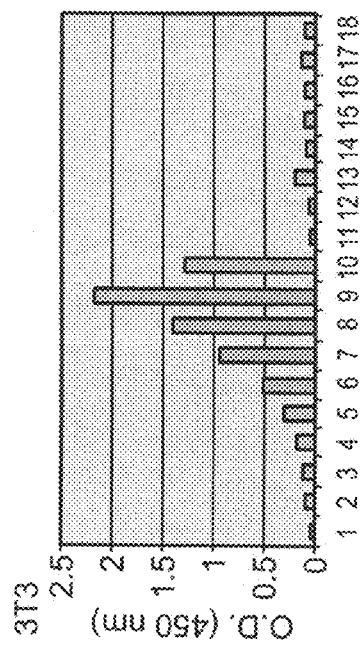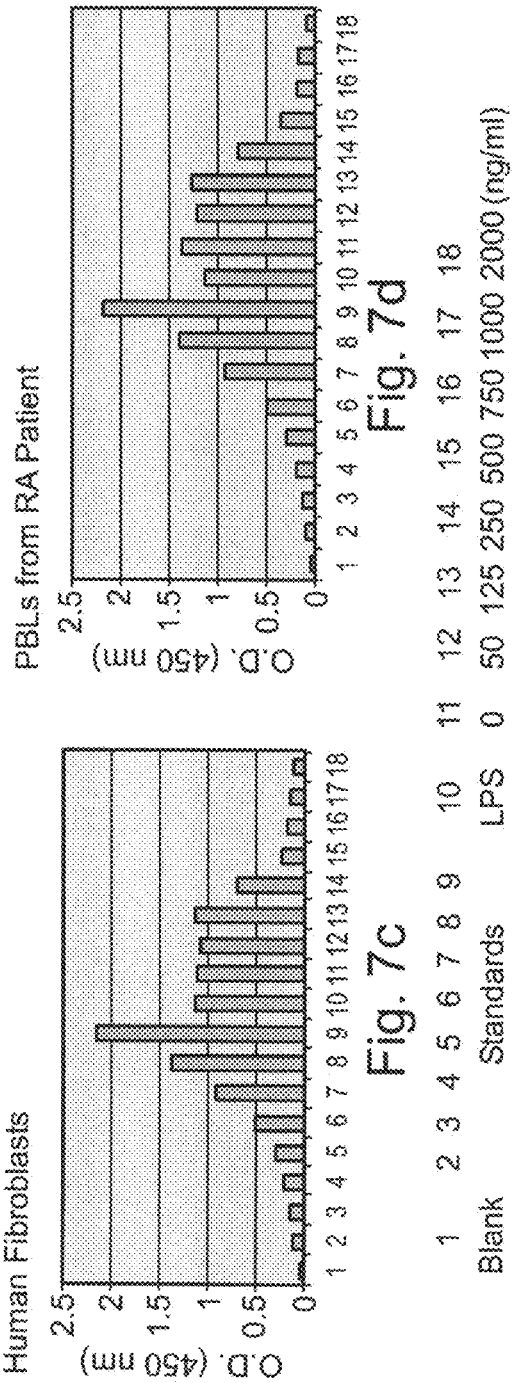

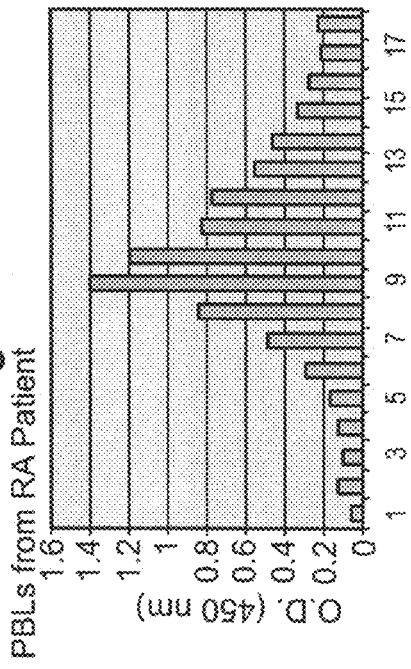
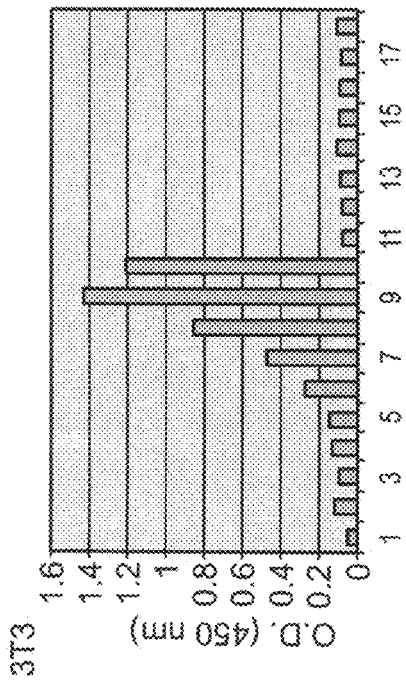
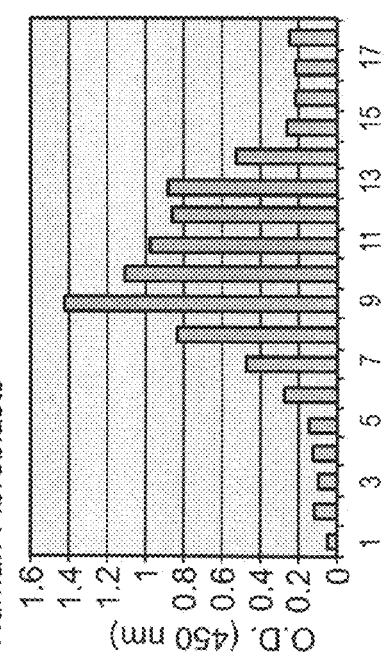
Fig. 8a, Fig. 8b, Fig. 8c, Fig. 8d

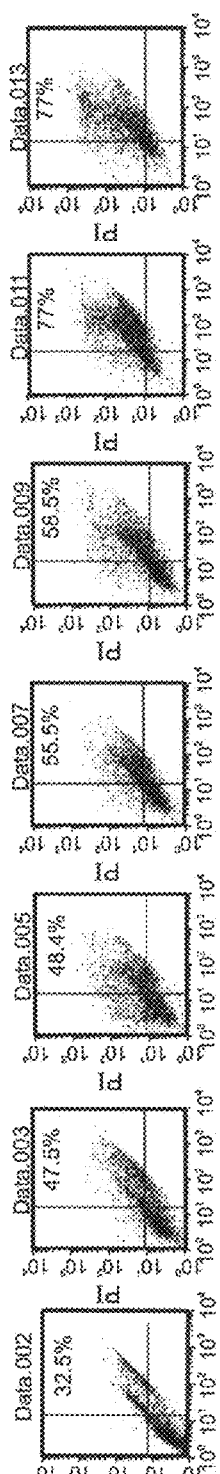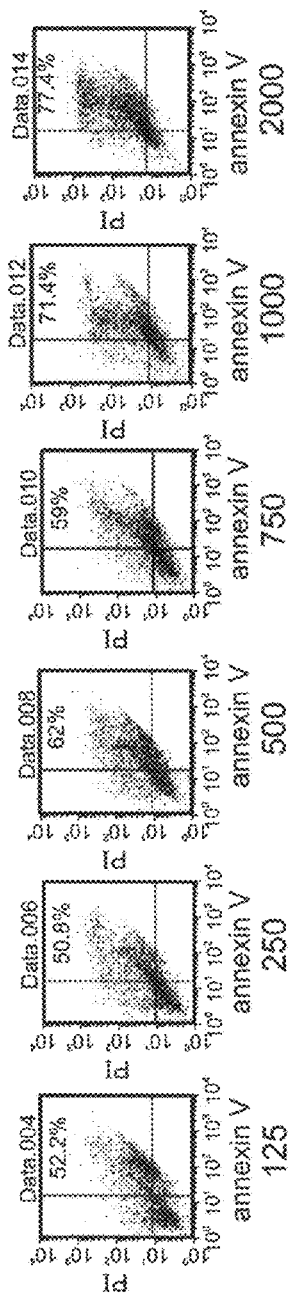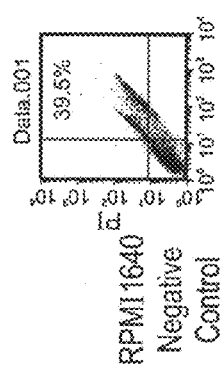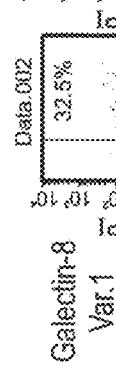
Fig. 11a Fig. 11b Fig. 11c Fig. 11d Fig. 11e Fig. 11f Fig. 11g Fig. 11h
Fig. 11i Fig. 11j Fig. 11k Fig. 11l Fig. 11m Fig. 11n
Galectin-8 var.1/var.2 Concentration (ng/ml)

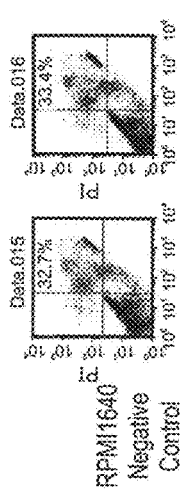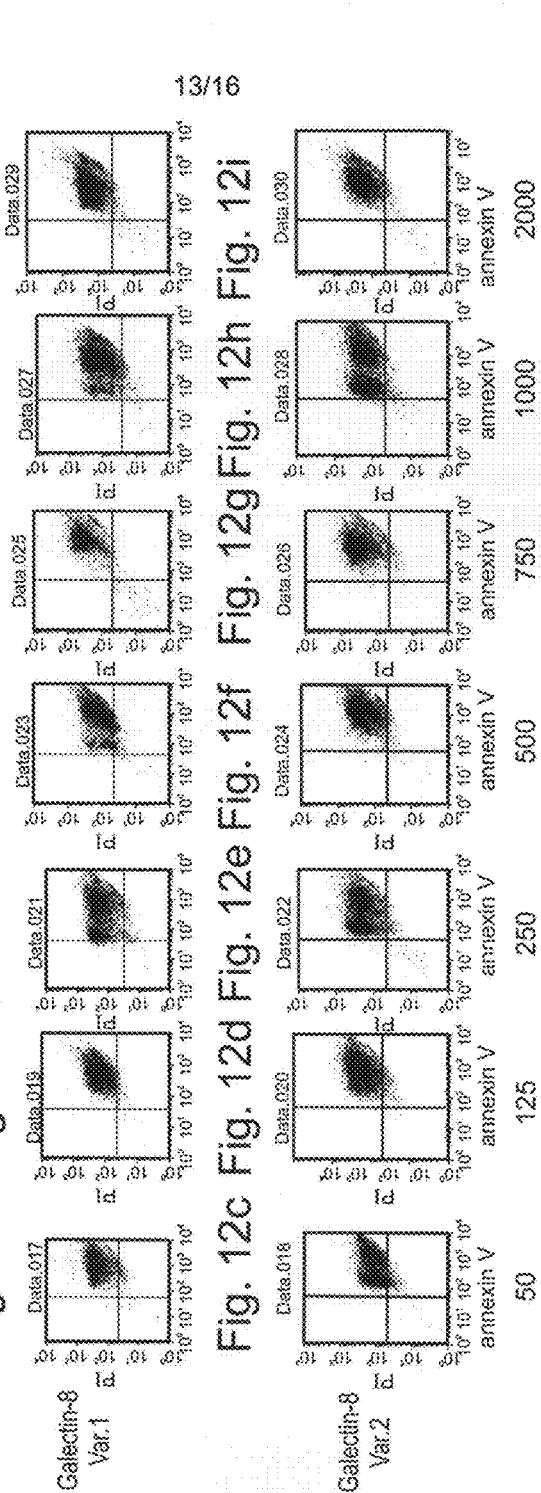
Fig. 12a Fig. 12b Fig. 12c Fig. 12d Fig. 12e Fig. 12f Fig. 12g Fig. 12h Fig. 12i Fig. 12j Fig. 12k Fig. 12l Fig. 12m Fig. 12n Fig. 12o Fig. 12p
Galectin-8 var.1/var.2 Concentration (ng/ml)

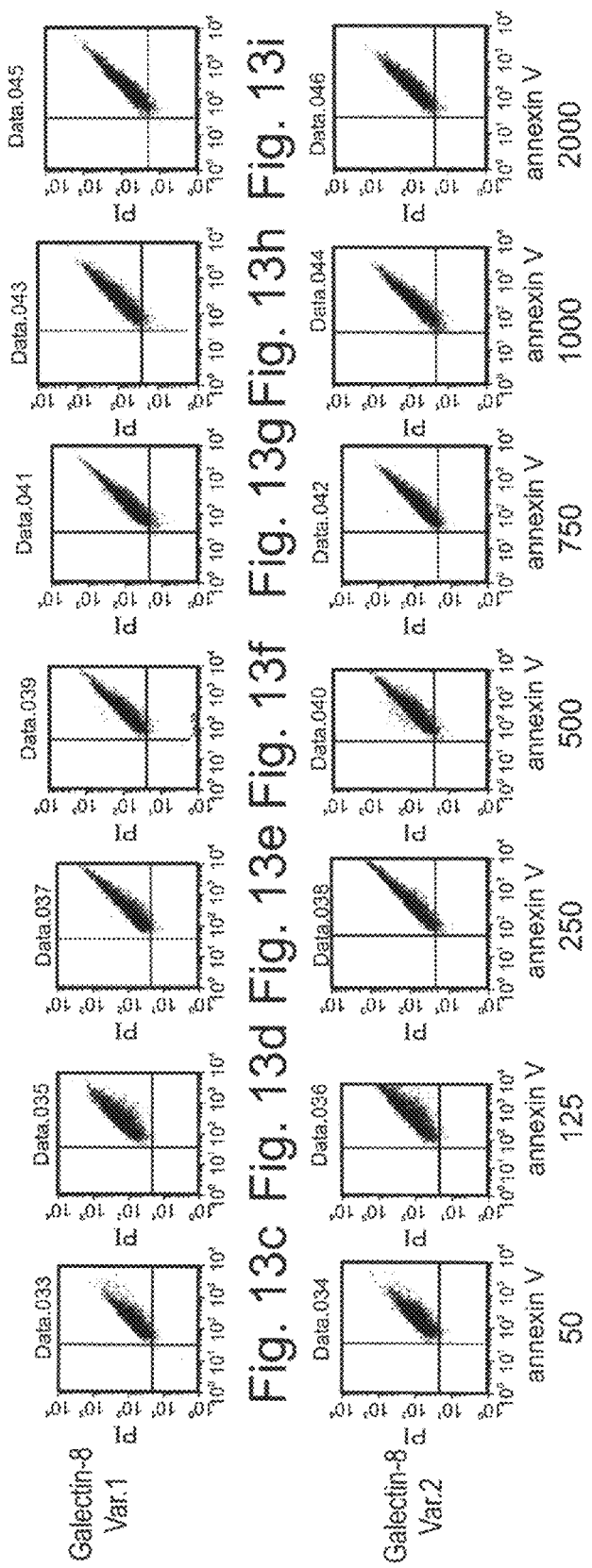

```
                              SEQUENCE LISTING

<160> NUMBER OF SEQ ID NOS: 18

<210> SEQ ID NO 1
<211> LENGTH: 35
<212> TYPE: DNA
<213> ORGANISM: Artificial sequence
<220> FEATURE:
<223> OTHER INFORMATION: Single strand DNA oligonucleotide

<400> SEQUENCE: 1
aagaattcgc cgccaccatg atgttgtcct taaac                                35

<210> SEQ ID NO 2
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 2
aatctagact accagctcct tacttc                                          26

<210> SEQ ID NO 3
<211> LENGTH: 2464
<212> TYPE: DNA
<213> ORGANISM: Homo sapiens

<400> SEQUENCE: 3
tggacttgga tccgaggcag acgaggaagc tgagaaaacc ctggcgttga ccccgtggac      60
ctgggcgccc cgggaaggtc cagcgcttgg tccaggcagg cggggatgtg cggtgaccac     120
cctggtcctg aaaagtccag ccccgaatct ccctcctcc tagacctgga ggcctggaac      180
agccagccgc ccacggacgc cagagccggg aaccctgacg gcacttagct gctgacaaac     240
aacctgctcc gtggacgcct gaaacaccag tctttggggc cagtgcctca gtttcaatcc     300
aggtaacctt taaatgaaac ttgcctaaaa tcttaggtca tacacagaag agactccaat     360
cgacaagaag ctggaaaaga atgatgttgt ccttaaacaa cctacagaat atcatctata     420
acccggtaat cccgtatgtt ggcaccattc ccgatcagct ggatcctgga actttgattg     480
```

```
tgatatgtgg gcatgttcct agtgacgcag acagattcca ggtggatctg cagaatggca    540
gcagtgtgaa acctcgagcc gatgtggcct tcatttcaa tcctcgtttc aaaagggccg     600
gctgcattgt ttgcaatact ttgataaatg aaaatgggg acgggaagag atcacctatg     660
acacgccttt caaagagaaa agtcttttg agatcgtgat tatggtgcta aaggacaaat     720
tccaggtggc tgtaaatgga aacatactc tgctctatgg ccacaggatc ggcccagaga     780
aaatagacac tctgggcatt tatggcaaag tgaatattca ctcaattggt tttagcttca    840
gctcggactt acaaagtacc caagcatcta gtctggaact gacagagata gtagagaaa     900
atgttccaaa gtctggcacg ccccagctta gcctgccatt cgctgcaagg ttgaacaccc    960
ccatgggccc tggacgaact gtcgtcgtta aggagaagt gaatgcaaat gccaaaagct     1020
ttaatgttga cctactagca ggaaaatcaa aggatattgc tctacacttg aacccacgcc    1080
tgaatattaa agcatttgta agaaattctt ttcttcagga gtcctgggga aagaagaga    1140
gaaatattac ctcttttccca tttagtcctg ggatgtactt tgagatgata atttactgtg    1200
atgttagaga attcaaggtt gcagtaaatg gcgtacacag cctggagtac aaacacagat    1260
ttaaagagct cagcagtatt gacacgctgg aaattaatgg agacatccac ttactggaag    1320
taaggagctg gtagcctacc tacacagctg ctacaaaaac caaaatacag aatggcttct    1380
gtgatactgg ccttgctgaa acgcatctca ctgtcattct attgtttata ttgttaaaat    1440
gagcttgtgc accattagat cctgctgggt gttctcagtc cttgccatga agtatggtgg    1500
tgtctagcac tgaatgggga aactgggggc agcaacactt atagccagtt aaagccactc    1560
tgccctctct cctactttgg ctgactcttc aagaatgcca ttcaacaagt atttatggag    1620
tacctactat aatacagtag ctaacatgta ttgagcacag atttttttg gtaaaactgt     1680
gaggagctag gatatatact tggtgaaaca aaccagtatg ttccctgttc tcttgagctt    1740
cgactcttct gtgctctatt gctgcgcact gcttttttcta caggcattac atcaactcct    1800
aaggggtcct ctgggattag ttaagcagct attaaatcac ccgaagacac taatttacag    1860
aagacacaac tccttcccca gtgatcactg tcataaccag tgctctaccg tatcccatca    1920
ctgaggactg atgttgactg acatcatttt atcgtaataa acatgtggct ctattagctg    1980
caagctttac caagtaattg gcatgacatc tgagcacaga aattaaggca aaaaaccaaa    2040
gcaaaacaaa tacatggtgc tgaaattaac ttgatgccaa gcccaaggca gctgatttct    2100
gtgtatttga acttagggca aatcagagtc tacacagacg cctacagaaa gtttcaggaa    2160
gaggcaagat gcattcaatt tgaaagatat ttatgggcaa caaagtaagg tcaggattag    2220
acttcaggca ttcataaggc aggcactatc agaaagtgta cgccaactaa gggacccaca    2280
aagcaggcag aggtaatgca gaaatctgtt ttgttcccat gaaatcacca atcaaggcct    2340
ccgttcttct aaagattagt ccatcatcat tagcaactga gatcaaagca ctcttccact    2400
ttacgtgatt aaaatcaaac ctgtatcagc aaaaaaaaaa aaaaaaaaaa aaaaaaaaa     2460
aaaa                                                                 2464
```

<210> SEQ ID NO 4
<211> LENGTH: 316
<212> TYPE: PRT
<213> ORGANISM: Homo sapiens

<400> SEQUENCE: 4

Met Leu Ser Leu Asn Asn Leu Gln Asn Ile Ile Tyr Asn Pro Val Ile
 1               5                  10                  15

Pro Tyr Val Gly Thr Ile Pro Asp Gln Leu Asp Pro Gly Thr Leu Ile

| | | 20 | | | 25 | | | 30 | | | |
|---|---|---|---|---|---|---|---|---|---|---|---|
|Val|Ile|Cys|Gly|His|Val|Pro|Ser|Asp|Ala|Asp|Arg|Phe|Gln|Val|Asp|

Val Ile Cys Gly His Val Pro Ser Asp Ala Asp Arg Phe Gln Val Asp
                    35                  40                  45
Leu Gln Asn Gly Ser Ser Val Lys Pro Arg Ala Asp Val Ala Phe His
 50                  55                  60
Phe Asn Pro Arg Phe Lys Arg Ala Gly Cys Ile Val Cys Asn Thr Leu
65                   70                  75                  80
Ile Asn Glu Lys Trp Gly Arg Glu Glu Ile Thr Tyr Asp Thr Pro Phe
                 85                  90                  95
Lys Arg Glu Lys Ser Phe Glu Ile Val Ile Met Val Leu Lys Asp Lys
             100                 105                 110
Phe Gln Val Ala Val Asn Gly Lys His Thr Leu Leu Tyr Gly His Arg
         115                 120                 125
Ile Gly Pro Glu Lys Ile Asp Thr Leu Gly Ile Tyr Gly Lys Val Asn
     130                 135                 140
Ile His Ser Ile Gly Phe Ser Phe Ser Ser Asp Leu Gln Ser Thr Gln
145                 150                 155                 160
Ala Ser Ser Leu Glu Leu Thr Glu Ile Ser Arg Glu Asn Val Pro Lys
                165                 170                 175
Ser Gly Thr Pro Gln Leu Ser Leu Pro Phe Ala Ala Arg Leu Asn Thr
            180                 185                 190
Pro Met Gly Pro Gly Arg Thr Val Val Lys Gly Glu Val Asn Ala
        195                 200                 205
Asn Ala Lys Ser Phe Asn Val Asp Leu Leu Ala Gly Lys Ser Lys Asp
    210                 215                 220
Ile Ala Leu His Leu Asn Pro Arg Leu Asn Ile Lys Ala Phe Val Arg
225                 230                 235                 240
Asn Ser Phe Leu Gln Glu Ser Trp Gly Glu Glu Arg Asn Ile Thr
                245                 250                 255
Ser Phe Pro Phe Ser Pro Gly Met Tyr Phe Glu Met Ile Ile Tyr Cys
            260                 265                 270
Asp Val Arg Glu Phe Lys Val Ala Val Asn Gly Val His Ser Leu Glu
        275                 280                 285
Tyr Lys His Arg Phe Lys Glu Leu Ser Ser Ile Asp Thr Leu Glu Ile
    290                 295                 300
Asn Gly Asp Ile His Leu Leu Glu Val Arg Ser Trp
305                 310                 315

<210> SEQ ID NO 5
<211> LENGTH: 657
<212> TYPE: DNA
<213> ORGANISM: Homo sapiens

<400> SEQUENCE: 5
atgatgttgt ccttaaacaa cctacagaat atcatctata acccggactt acaaagtacc      60
caagcatcta gtctggaact gacagagata gtagagaaa atgttccaaa gtctggcacg     120
ccccagcttc ctagtaatag aggagggac atttctaaaa tcgcacccag aactgtctac     180
accaagagca agaggcgag gcaatcacac tttgacttgc accaaaatac cacctatgaa     240
ctatgtgtca gagcctgcc attcgctgca aggttgaaca cccccatggg ccctggacga     300
actgtcgtcg ttaaaggaga agtgaatgca aatgccaaaa gctttaatgt tgacctacta     360
gcaggaaaat caaggatat tgctctacac ttgaacccac gctgaatat taaagcattt     420
gtaagaaatt cttttcttca ggagtcctgg ggagaagaag agagaaatat tacctctttc     480

```
ccatttagtc ctgggatgta ctttgagatg ataatttact gtgatgttag agaattcaag      540
gttgcagtaa atggcgtaca cagcctggag tacaaacaca gatttaaaga gctcagcagt      600
attgacacgc tggaaattaa tggagacatc cacttactgg aagtaaggag ctggtag         657
```

<210> SEQ ID NO 6
<211> LENGTH: 218
<212> TYPE: PRT
<213> ORGANISM: Homo sapiens

<400> SEQUENCE: 6

```
Met Met Leu Ser Leu Asn Asn Leu Gln Asn Ile Ile Tyr Asn Pro Asp
 1               5                  10                  15

Leu Gln Ser Thr Gln Ala Ser Ser Leu Glu Leu Thr Glu Ile Ser Arg
             20                  25                  30

Glu Asn Val Pro Lys Ser Gly Thr Pro Gln Leu Pro Ser Asn Arg Gly
         35                  40                  45

Gly Asp Ile Ser Lys Ile Ala Pro Arg Thr Val Tyr Thr Lys Ser Lys
     50                  55                  60

Glu Ala Arg Gln Ser His Phe Asp Leu His Glu Asn Thr Thr Tyr Glu
 65                  70                  75                  80

Leu Cys Val Lys Ser Leu Pro Phe Ala Ala Arg Leu Asn Thr Pro Met
                 85                  90                  95

Gly Pro Gly Arg Thr Val Val Lys Gly Glu Val Asn Ala Asn Ala
            100                 105                 110

Lys Ser Phe Asn Val Asp Leu Leu Ala Gly Lys Ser Lys Asp Ile Ala
        115                 120                 125

Leu His Leu Asn Pro Arg Leu Asn Ile Lys Ala Phe Val Arg Asn Ser
    130                 135                 140

Phe Leu Gln Glu Ser Trp Gly Glu Glu Arg Asn Ile Thr Ser Phe
145                 150                 155                 160

Pro Phe Ser Pro Gly Met Tyr Phe Glu Met Ile Ile Tyr Cys Asp Val
                165                 170                 175

Arg Glu Phe Lys Val Ala Val Asn Gly Val His Ser Leu Glu Tyr Lys
            180                 185                 190

His Arg Phe Lys Glu Leu Ser Ser Ile Asp Thr Leu Glu Ile Asn Gly
        195                 200                 205

Asp Ile His Leu Leu Glu Val Arg Ser Trp
    210                 215
```

<210> SEQ ID NO 7
<211> LENGTH: 669
<212> TYPE: DNA
<213> ORGANISM: Homo sapiens

<400> SEQUENCE: 7

```
atgatgttgt ccttaaacaa cctacagaat atcatctata acccggtaat cccgtatgtt       60
ggcaccattc ccgatcagct ggatcctgga actttgattg tgatatgtgg gcatgttcct      120
agtgacgcag acagattcca ggtggatctg cagaatggca gcagtgtgaa acctcgagcc      180
gatgtggcct tcatttcaa tcctcgtttc aaaagggccg gctgcattgt ttgcaatact      240
ttgataaatg aaaatgggg acggaagag atcacctatg acacgccttt caaaagagaa      300
aagtcttttg agatcgtgat tatggtgcta aaggacaaat tccaggactt acaaagtacc      360
caagcatcta gtctggaact gacagagata agtagagaaa atgttccaaa gtctggcacg      420
ccccagctta gcctgccatt cgctgcaagg ttgaacaccc ccatgggccc tggacgaact      480
```

```
gtcgtcgtta aagtgagaag tgaatgcaaa tgccaaaaga tgataattta ctgtgatgtt      540
agagaattca aggttgcagt aaatggcgta cacagcctgg agtacaaaca cagatttaaa      600
gagctcagca gtattgacac gctggaaatt aatggagaca tccacttact ggaagtaagg      660
agctggtag                                                              669
```

<210> SEQ ID NO 8
<211> LENGTH: 222
<212> TYPE: PRT
<213> ORGANISM: Homo sapiens
<400> SEQUENCE: 8

```
Met Met Leu Ser Leu Asn Asn Leu Glu Asn Ile Ile Tyr Asn Pro Tyr
1               5                   10                  15

Ile Pro Tyr Val Gly Thr Ile Pro Asp Gln Leu Asp Pro Gly Thr Leu
            20                  25                  30

Ile Val Ile Cys Gly His Val Pro Ser Asp Ala Asp Arg Phe Gln Val
        35                  40                  45

Asp Leu Gln Asn Gly Ser Ser Val Lys Pro Arg Ala Asp Val Ala Phe
    50                  55                  60

His Phe Asn Pro Arg Phe Lys Arg Ala Gly Cys Ile Val Cys Asn Thr
65                  70                  75                  80

Leu Ile Asn Glu Lys Trp Gly Arg Glu Glu Ile Thr Tyr Asp Thr Pro
                85                  90                  95

Phe Lys Arg Glu Lys Ser Phe Glu Ile Val Ile Met Val Leu Lys Asp
            100                 105                 110

Lys Phe Gln Asp Leu Gln Ser Thr Gln Ala Ser Ser Leu Glu Leu Thr
        115                 120                 125

Glu Ile Ser Arg Glu Asn Val Pro Lys Ser Gly Thr Pro Gln Leu Ser
    130                 135                 140

Leu Pro Phe Ala Ala Arg Leu Asn Thr Pro Met Gly Pro Gly Arg Thr
145                 150                 155                 160

Val Val Val Lys Val Arg Ser Glu Cys Lys Cys Gln Lys Met Ile Ile
                165                 170                 175

Tyr Cys Asp Val Arg Glu Phe Lys Val Ala Val Asn Gly Val His Ser
            180                 185                 190

Leu Glu Tyr Lys His Arg Phe Lys Glu Leu Ser Ser Ile Asp Thr Leu
        195                 200                 205

Glu Ile Asn Gly Asp Ile His Leu Leu Glu Val Arg Ser Trp
    210                 215                 220
```

<210> SEQ ID NO 9
<211> LENGTH: 26
<212> TYPE: DNA
<213> ORGANISM: Artificial sequence
<220> FEATURE:
<223> OTHER INFORMATION: Single strand DNA oligonucleotide
<400> SEQUENCE: 9

```
gcaaatgcca aaagatgata atttac                                           26
```

<210> SEQ ID NO 10
<211> LENGTH: 24
<212> TYPE: DNA
<213> ORGANISM: Artificial sequence
<220> FEATURE:
<223> OTHER INFORMATION: Single strand DNA oligonucleotide
<400> SEQUENCE: 10

```
ggacaaattc caggacttac aaag                                            24

<210> SEQ ID NO 11
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 11
cctctagaat gatgttgtcc ttaaac                                          26

<210> SEQ ID NO 12
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 12
gccatatgct accagctcct tacttc                                          26

<210> SEQ ID NO 13
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 13
cctctagaat gatgttgtcc ttaaac                                          26

<210> SEQ ID NO 14
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 14
gccatatgct accagctcct tacttc                                          26

<210> SEQ ID NO 15
<211> LENGTH: 660
<212> TYPE: DNA
<213> ORGANISM: Homo sapiens

<400> SEQUENCE: 15
atgatgttgt ccttaaacaa cctacagaat atcatctata acccggactt acaaagtacc     60
caagcatcta gtctggaact gacagagata agtagagaaa atgttccaaa gtctggcacg    120
ccccagcttc ctagtaatag aggaggagac atttctaaaa tcgcacccag aactgtctac    180
accaagagca agattcgac tgtcaatcac actttgactt gcaccaaaat accacctatg     240
aactatgtgt caaagagcct gccattcgct gcaaggttga cacccccat gggccctgga     300 cgaactgtcg tcgttaaagg agaagtgaat gcaaatgcca aaagctttaa tgttgaccta    360
ctagcaggaa aatcaaagga tattgctcta cacttgaacc cacgcctgaa tattaaagca    420
tttgtaagaa attctttct tcaggagtcc tggggagaag aagagagaaa tattacctct    480 ttcccatttta gtcctgggat gtactttgag atgataattt actgtgatgt tagagaattc    540
aaggttgcag taaatggcgt acacagcctg gagtacaaac acagatttaa agagctcagc    600
agtattgaca cgctggaaat taatggagac atccacttac tggaagtaag gagctggtag    660
```

```
<210> SEQ ID NO 16
<211> LENGTH: 219
<212> TYPE: PRT
<213> ORGANISM: Homo sapiens

<400> SEQUENCE: 16

Met Met Leu Ser Leu Asn Asn Leu Gln Asn Ile Ile Tyr Asn Pro Asp
1               5                   10                  15

Leu Gln Ser Thr Gln Ala Ser Ser Leu Glu Leu Thr Glu Ile Ser Arg
            20                  25                  30

Glu Asn Val Pro Lys Ser Gly Thr Pro Gln Leu Pro Ser Asn Arg Gly
        35                  40                  45

Gly Asp Ile Ser Lys Ile Ala Pro Arg Thr Val Tyr Thr Lys Ser Lys
    50                  55                  60

Asp Ser Thr Val Asn His Thr Leu Thr Cys Thr Lys Ile Pro Pro Met
65                  70                  75                  80

Asn Tyr Val Ser Lys Ser Leu Pro Phe Ala Ala Arg Leu Asn Thr Pro
                85                  90                  95

Met Gly Pro Gly Arg Thr Val Val Lys Gly Glu Val Asn Ala Asn
            100                 105                 110

Ala Lys Ser Phe Asn Val Asp Leu Leu Ala Gly Lys Ser Lys Asp Ile
        115                 120                 125

Ala Leu His Leu Asn Pro Arg Leu Asn Ile Lys Ala Phe Val Arg Asn
    130                 135                 140

Ser Phe Leu Gln Glu Ser Trp Gly Glu Glu Arg Asn Ile Thr Ser
145                 150                 155                 160

Phe Pro Phe Ser Pro Gly Met Tyr Phe Glu Met Ile Ile Tyr Cys Asp
                165                 170                 175

Val Arg Glu Phe Lys Val Ala Val Asn Gly Val His Ser Leu Glu Tyr
            180                 185                 190

Lys His Arg Phe Lys Glu Leu Ser Ser Ile Thr Leu Glu Ile Asn
        195                 200                 205

Gly Asp Ile His Leu Leu Glu Val Arg Ser Trp
    210                 215

<210> SEQ ID NO 17
<211> LENGTH: 72
<212> TYPE: DNA
<213> ORGANISM: Homo sapiens
<220> FEATURE:
<221> NAME/KEY: misc_feature
<223> OTHER INFORMATION: A polynucleotide expressing a unique portion of
      galectin-8 1.1 variant

<400> SEQUENCE: 17
gattcgactg tcaatcacac tttgacttgc accaaaatac cacctatgaa ctatgtgtca      60
aagagcctgc ca                                                         72

<210> SEQ ID NO 18
<211> LENGTH: 24
<212> TYPE: PRT
<213> ORGANISM: Homo sapiens
<220> FEATURE:
<221> NAME/KEY: misc_feature
<223> OTHER INFORMATION: A unique sequence portion of galectin-8 1.1
      variant

<400> SEQUENCE: 18

Asp Ser Thr Val Asn His Thr Leu Thr Cys Thr Lys Ile Pro Pro Met
1               5                   10                  15
```

```
Asn Tyr Val Ser Lys Ser Leu Pro
            20
```

GALECTIN SEQUENCES AND COMPOSITIONS AND METHODS UTILIZING SAME FOR TREATING OR DIAGNOSING ARTHRITIS AND OTHER CHRONIC INFLAMMATORY DISEASES

RELATED APPLICATIONS

This application is a National Phase of PCT Patent Application No. PCT/IL2006/000548 having International Filing Date of May 9, 2006, which is a continuation of U.S. patent application Ser. No. 11/125,263 filed on May 10, 2005, now abandoned, which is a continuation-in-part of PCT Patent Application No. PCT/IL03/00960 having International Filing Date of Nov. 13, 2003, which claims the benefit of priority of U.S. Provisional Patent Application No. 60/428,691 filed on Nov. 25, 2002 and of U.S. Provisional Patent Application No. 60/426,041 filed on Nov. 14, 2002. The contents of the above applications are all incorporated herein by reference.

This application is also a continuation-in-part (CIP) of U.S. patent application Ser. No. 11/907,893 filed on Oct. 18, 2007, now abandoned.

FIELD AND BACKGROUND OF THE INVENTION

The present invention relates to novel galectin sequences and use thereof in treatment or diagnosis of arthritis and other chronic inflammatory diseases.

Rheumatoid Arthritis (RA) is a chronic, systemic inflammatory disease primarily involving the joints. It affects 1-3% of the population with a female to male ratio of 3:1. Constitutional symptoms may include malaise, fever and weight loss. The disease characteristically begins in the small joints of the hands and feet, usually progressing in a centripetal and symmetric fashion. Deformation of joints and disability are very common, but the disease may also decrease expected life span by an average of ~9 years in the more active forms. Extra-articular manifestations of the rheumatoid process may cause significant morbidity and include vasculitis, atrophy of the skin and muscle, subcutaneous nodules, lymphadenopathy, splenomegaly and leukopenia, neuropathy, cervical myelopathy, ophthalmic complications, Sjogren syndrome, lung and heart involvement and amyloidosis.

The inflammation of the synovial joints characterizing RA is the result of hyperplasia of synovial fibroblasts and infiltration of lymphocytes, macrophages and plasma cells, all of which manifest signs of activation. These cells proliferate abnormally, invade bone and cartilage, produce an elevated amount of pro-inflammatory cytokines, metalloproteinases and trigger osteoclast formation and activation. Some of the pathophysiological consequences of the disease are explained by inadequate apoptosis, which may promote the survival of autoreactive T cells, macrophages or synovial fibroblasts [Rabinovich G. A., Mem Inst Oswaldo Cruz., 95:225, (2000)].

Selective therapeutic targeting of pathological cells, such as inflammatory cells is a major challenge for modern medicine. Differences in cell surface molecules or signal transduction pathways between pathological cells and their normal counterparts can be used as a handle for selective destruction of the former. Unfortunately, the existence of such discrete target entities in pathological cells is not an obvious phenomenon.

Discrimination between "harmful" inflammatory cells, involved in self-destruction, and inflammatory cells engaged in the eradication of microorganisms is complicated, because there is no indication that the two cell types differ chemically or biologically. The discriminatory elements might be found in the T cell receptor (TCR) of those cells initiating the inflammatory cascade or in the corresponding major histocompatibility (MHC) sequences of antigen presenting cells (APCs), which bind the relevant peptide. Unfortunately, targeting of TCR or MHC molecules would be effective only at the initial phase of autoimmune diseases, when the symptoms are still undetectable. Consequently, in many cases this approach may be impractical.

A different tactic is to target pro-inflammatory molecules that are involved in more progressive stages of the process, when there is a non-specific influx of leukocytes, attracted by chemokines and activated by cytokines. Indeed, it has been shown that autoimmune diseases can be controlled by targeting inflammation-supportive molecules, such as selecting, integrins, IL-12, TNFα and NFkB, using specific antibodies or anti-sense oligonucleotide [Taylor P. C., Curr. Pharm. Des., 9:1095, (2003); Kevorkov N. N. and Futlik D. M., Russ. J. Immunol., 5:5, (2000); Louie S. G., et al. Am. J. Health Syst. Pharm. 60:346, (2003)].

However, the same molecules are also involved in essential physiological functions and, therefore, it is unpredictable when and how the price of such "nonspecific" therapy will be exacted.

There is thus a widely recognized need for restricted targeting inflammation-supportive molecules and it would be highly advantageous to identify pro-inflammatory molecules, involved in a relatively late phase of the process that displays sufficient chemical diversity to allow restricted targeting. The novel galectin isoforms presented here may meet these requirements.

Galectins comprise a family of proteins that are widely expressed in mammals. All galectins share the ability to bind β-galactosides through an evolutionarily conserved sequence motif in the carbohydrate-binding site (1). They have a cytoplasmic or nuclear localization and despite of lack of signal peptide, they can be externalized as soluble proteins by non-classical secretory mechanisms (2, 3). In mammals, ten galectins have been characterized (3, 4). Two groups of galectins are distinguished according to the number of lectin domains. Most of them, including galectin-1, 2, 3, 5, 7 and 10, have a single lectin domain. Galectin-4, 6, 8 and 9 belong to the second group and are characterized by two lectin domains linked by a hinged peptide (4-7).

The exact role(s) of galectins is not clearly established, but they are suspected to modulate several cellular functions such as physiological (8) and malignant cell adhesion, cell proliferation (9), apoptosis (10), metastasis seeding (11) and immune function (12, 13). They have also been described as nuclear proteins (14) possibly involved in pre-messenger RNA splicing (15, 16). Expression analysis has revealed a broad distribution in healthy tissues for galectin-1, 3, 4, 8 and 9, while galectin-2, 5, 6 or 7 are restricted mainly to one specific tissue (such as lung, prostate etc., 16 17). Differential expression of these proteins has been well documented in the literature in healthy tissues or in tumor cells (9, 11, 18).

The present inventors have previously uncovered that galectin-8 and variants thereof are capable of reducing the inflammatory response in human synovial tissue due to their ability to inhibit the release of the pro-inflammatory cytokines TNF-α and IL-1β, to increase the production of the anti-inflammatory cytokine IL-1ra and to induce apoptosis in synovial fluid cells (see PCT Appl. No. IL03/00960).

While reducing the present invention to practice, the present inventors have identified novel isoforms of human galectins which are specific to synovial fluid cells of RA

SUMMARY OF THE INVENTION

According to one aspect of the present invention there is provided an isolated polynucleotide comprising a nucleic acid sequence encoding a galectin-8 variant polypeptide having an amino acid sequence coordinates 65-88 of SEQ ID NO: 16.

According to further features in preferred embodiments of the invention described below, the isolated polynucleotide as set forth in SEQ ID NO: 15 or 17.

According to another aspect of the present invention there is provided an isolated polypeptide comprising an amino acid sequence as set forth in SEQ ID NO: 16 or 18.

According to yet another aspect of the present invention there is provided a pharmaceutical composition, comprising, as an active ingredient, the isolated polypeptide and at least one type of a disease-modifying antirheumatic drug (DMARD) and a pharmaceutically acceptable carrier.

According to still further features in the described preferred embodiments the at least one type of a disease-modifying antirheumatic drug is selected from the group consisting of auranofin, azathioprine, cyclophosphamide, cyclosporine, gold sodium thiomalate, hydroxychloro-quine sulfate, leflunomide, methotrexate, minocycline, penicillamine, sulfasalazine, etanercept, infliximab, anakinra and adalimumab.

According to still another aspect of the present invention there is provided a pharmaceutical composition, comprising, as an active ingredient, the isolated polypeptide and at least one type of a nonsteroidal anti-inflammatory drug (NTHE) and a pharmaceutically acceptable carrier.

According to still further features in the described preferred embodiments the at least one type of a nonsteroidal anti-inflammatory drug (NTHE) is selected from the group consisting of diclofenac potassium, diclofenac sodium, diclofenac sodium with misoprostol, diflunisal, etodolac, fenoprofen calcium, flurbiprofen, ibuprofen, indomethacin, ketoprofen, meclofenamate sodium, mefenamic acid, meloxicam, nabumetone, naproxen, naproxen sodium, oxaprozin, piroxicam, sulindac, tolmetin sodium, celecoxib, rofecoxib, valdecoxib, aspirin, choline and magnesium salicylates, choline salicylate, magnesium salicylate, salsalate, sodium salicylate, cortisone, dexamethasone, hydrocortisone, methylprednisolone, prednisolone, prednisolone sodium phosphate and prednisone.

According to an additional aspect of the present invention there is provided a pharmaceutical composition, comprising, as an active ingredient, the isolated polypeptide and a pharmaceutically acceptable carrier.

According to yet an additional aspect of the present invention there is provided a pharmaceutical composition, comprising, as an active ingredient, the isolated polynucleotide and a pharmaceutically acceptable carrier.

According to still an additional aspect of the present invention there is provided an article-of-manufacture comprising packaging material and a pharmaceutical composition identified for reducing inflammatory response, being contained within the packaging material, the pharmaceutical composition including, as an active ingredient, the isolated polypeptide and a pharmaceutically acceptable carrier.

According to a further aspect of the present invention there is provided an article-of-manufacture comprising packaging material and a pharmaceutical composition identified for reducing inflammatory response, being contained within the packaging material, the pharmaceutical composition including, as an active ingredient, the isolated polynucleotide and a pharmaceutically acceptable carrier.

According to yet a further aspect of the present invention there is provided a method of reducing inflammatory response in an individual, comprising providing to the individual a therapeutically effective amount of the isolated polypeptide, thereby reducing the inflammatory response in the individual.

According to still further features in the described preferred embodiments the providing is effected by expressing the polypeptide within cells of the individual.

According to still further features in the described preferred embodiments the cells of the individual are synovial fluid cells.

According to still further features in the described preferred embodiments the providing is effected by administration of a pharmaceutical composition comprising the isolated polypeptide.

According to still further features in the described preferred embodiments the administration is oral, injection or topical administration.

According to still further features in the described preferred embodiments the administration by injection is direct injection into a joint of the individual.

According to still further features in the described preferred embodiments the providing is effected by:
(i) isolating synovial fluid cells from the individual;
(ii) transforming the synovial fluid cells with an expression construct capable of expressing the isolated polypeptide in the synovial fluid cells; and
(iii) administering the synovial fluid cells resultant from step (b) into the individual.

According to still a further aspect of the present invention there is provided a population of cells comprising synovial fluid cells transformed to express the isolated polypeptide.

According to still a further aspect of the present invention there is provided a nucleic acid construct comprising the polynucleotide.

According to still further features in the described preferred embodiments the method further comprising a promoter for regulating expression of the polynucleotide.

According to still a further aspect of the present invention there is provided a cell comprising the nucleic acid construct.

According to still a further aspect of the present invention there is provided a method of detecting an inflammatory response in an individual comprising identifying in biological sample obtained from the individual a transcription and/or translation product of the galectin-8 variant, wherein a presence of the transcription and/or translation product is indicative of an inflammatory response.

According to still further features in the described preferred embodiments the biological sample is the synovial fluid cells.

According to still a further aspect of the present invention there is provided a method of diagnosing an individual having an inflammatory disease comprising:
(a) obtaining a biological sample from the individual; and
(b) detecting in the biological sample a transcription and/or translation product of the galectin-8 variant, wherein a presence of the transcription and/or translation product indicates presence of an inflammatory disease.

According to still further features in the described preferred embodiments the biological sample includes synovial fluid cells.

According to still a further aspect of the present invention there is provided a pair of oligonucleotides capable of directing PCR amplification of a polynucleotide sequence encoding the isolated polypeptide and not the polypeptides set forth in SEQ ID NO: 4, 6 and 8.

According to still further features in the described preferred embodiments the pair of oligonucleotides are set forth in SEQ ID NOS: 13 and 14.

According to still a further aspect of the present invention there is provided a kit for diagnosing RA patients comprising at least one pair of the oligonucleotides and reagents for detecting a PCR product.

According to still a further aspect of the present invention there is provided a polynucleotide probe comprising a nucleic acid sequence specifically hybridizable with a polynucleotide sequence encoding the isolated polynucleotide and not the galectin-8 as set forth in SEQ ID NO: 3, 5 or 7.

According to still further features in the described preferred embodiments the polynucleotide sequence encoding galectin-8 variant is SEQ ID NO: 15 or 17.

According to still a further aspect of the present invention there is provided a kit for diagnosing RA patients comprising at least one polynucleotide probe and reagents for detecting a hybridization product.

According to still further features in the described preferred embodiments the at least one polynucleotide probe is labeled with a detectable moiety.

According to still further features in the described preferred embodiments the detectable moiety is selected from the group consisting of a chromogenic moiety, a fluorogenic moiety, a light-emitting moiety and a radioactive moiety.

According to still a further aspect of the present invention there is provided an antibody comprising an antigen recognition region capable of specifically binding the isolated polypeptide and not an isolated polypeptide as set forth in SEQ ID NO: 4 or 8.

According to still a further aspect of the present invention there is provided a kit for diagnosing RA patients, comprising the antibody and reagents for detecting antibody binding.

According to still further features in the described preferred embodiments the polynucleotide probe is labeled with a detectable moiety.

According to still further features in the described preferred embodiments the detectable moiety is selected from the group consisting of a chromogenic moiety, a fluorogenic moiety, a light-emitting moiety and a radioactive moiety.

The present invention successfully addresses the shortcomings of the presently known configurations by providing novel approaches for treatment or diagnosis of inflammatory diseases.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a schematic illustration of variants 1, 2 and 3 of galectin-8 with respect to galectin-8 transcript (SEQ ID NO: 3)

Figure 1:
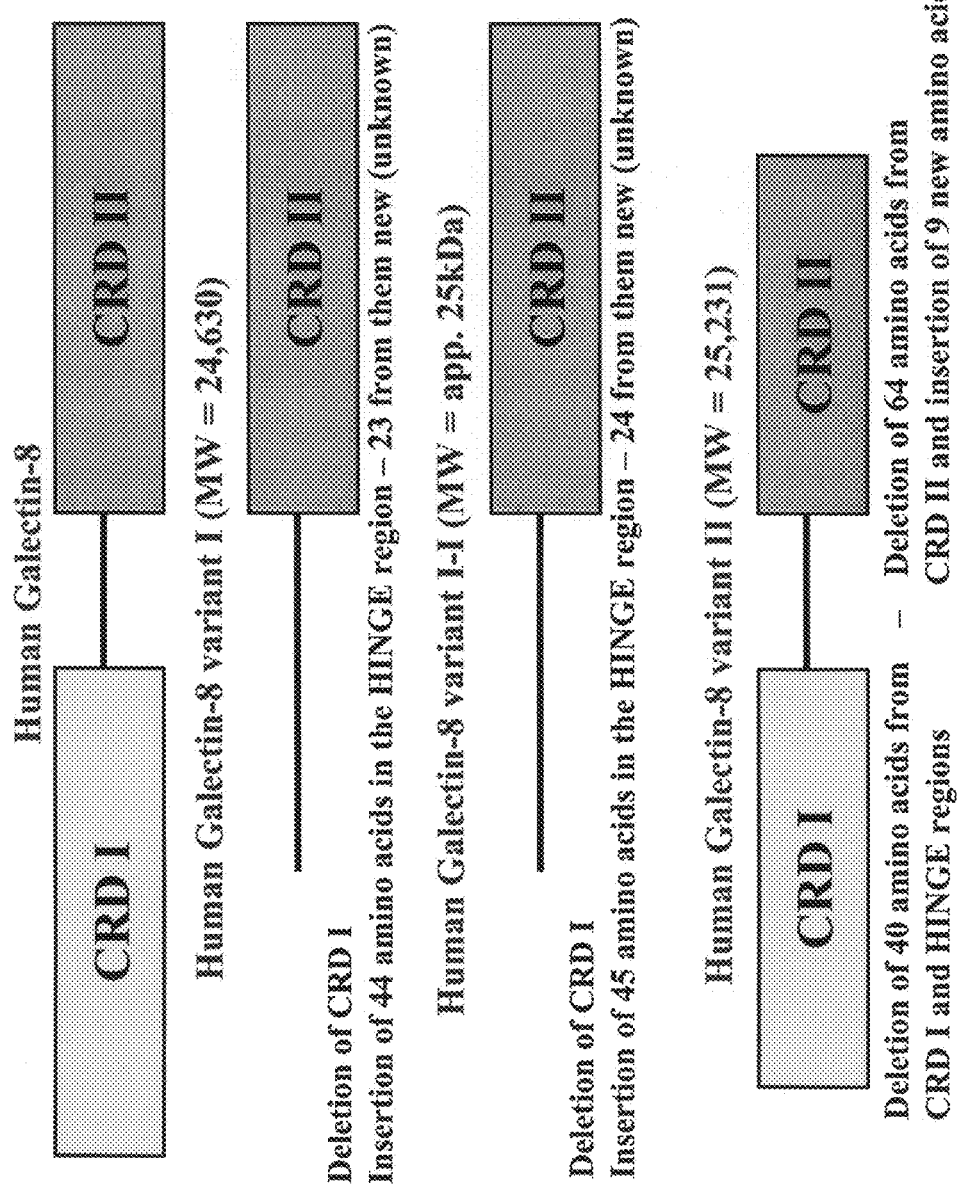
Figure 2:
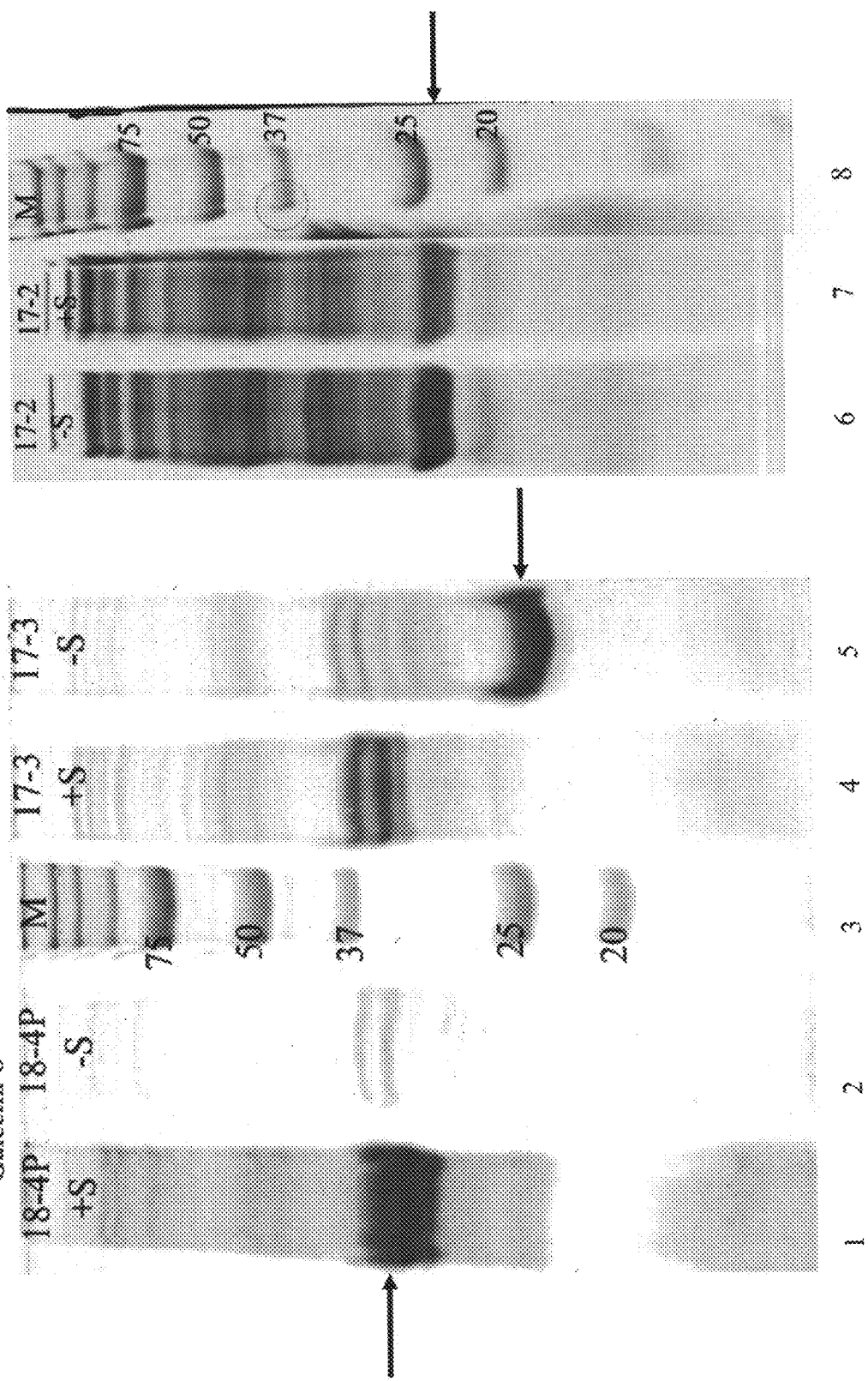

FIG. 2 is a photograph of a 7.5% acrylamide-SDS protein gel stained with Commassie blue demonstrating the presence of recombinant galectin polypeptides. Lanes 3 and 8 are protein molecular weight markers. Recombinant galectin-8 polypeptide (r-Gal-8) (SEQ ID NO: 4) was run prior to (lane 2) and following (lane 1) lactosyl sepharose purification. Recombinant galectin-8 variant 2 polypeptide (SEQ ID NO: 8) was run prior to (lane 5) and following (lane 4) lactosyl sepharose purification. Recombinant galectin-8 variant 1 (SEQ ID NO: 6) polypeptide was run prior to (lane 7) and following (lane 8) lactosyl sepharose purification.

FIGS. 3a-b are plot graphs depicting the binding of anti-galectin-8 antibodies to synovial fluid cells and blood cells of arthritic patients as measured by FACS analysis. FIG. 3a demonstrates the presence of galectin-8 in synovial fluid cells (pink line). FIG. 3b demonstrates the absence of galectin-8 from peripheral blood cells (pink line). Following addition of recombinant galectin-8, the anti-galectin-8 antibody binds to both synovial fluid and peripheral blood cells (orange lines).

Figure 4:
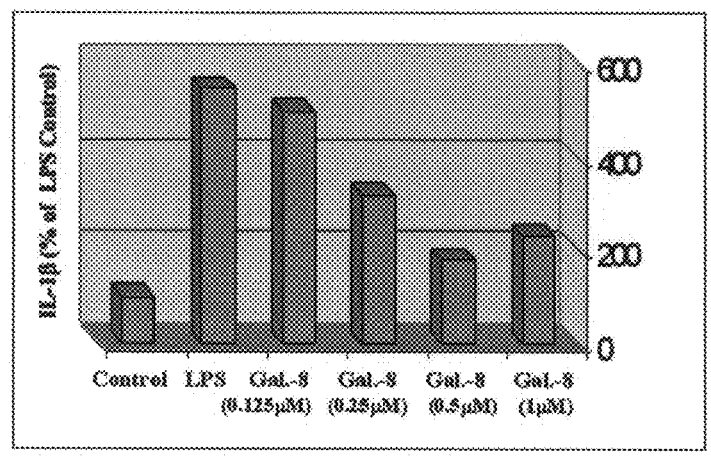

FIG. 4 is a bar graph depicting the effect of recombinant polypeptide galectin-8 (SEQ ID NO: 4) on IL-1β levels found in synovial tissue culture medium supplemented with 3 μg/ml lipopolysaccharide (LPS). The bars compare the IL-1β levels (as a percentage of the IL-1β level in LPS treated control) in media of synovial tissue cultures supplemented with various concentrations of galectin-8 (0.125 μM, 0.25 μM, 0.5 μM and 1 μM), following 48 hours of incubation. Data was collected using the quantified human immunoassay technique (see Example 5 for further details). The graph shows a decrease of IL-1β levels in media of synovial tissue cultures supplemented with galectin-8 as compared with IL-1β level in medium of cells with no galectin-8 addition (LPS). Addition of 0.125 μM (GAL 0.125 μM), 0.25 μM (GAL 0.25 μM) and 0.5 μM (GAL 0.5 μM) galectin-8 leads to approximately 9%, 42% and 67% decrease of IL-1β levels respectively, verifying that the effect of galectin-8 on IL-1β levels is dose dependent.

Figure 5:
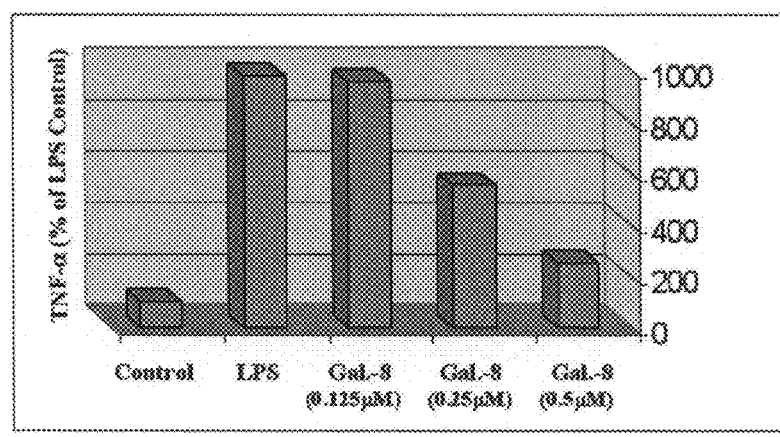

FIG. 5 is a bar graph depicting the effect of recombinant polypeptide galectin-8 (SEQ ID NO: 4) on TNFα levels in media of synovial tissue cultures supplemented with 3 μg/ml lipopolysaccharide (LPS). The bars compare TNFα levels (as a percentage of the TNFα level in LPS treated control) in media of synovial tissue cultures supplemented with increasing concentrations of galectin-8 (0.125 μM, 0.25 μM and 0.5 μM), following 48 hours of incubation. Data was collected using the quantified human immunoassay technique (see Example 5 for further details). The graph shows a decrease of TNFα levels in media of synovial tissue cultures supplemented with galectin-8 as compared with TNFα level in medium of cells with no galectin-8 addition (LPS). Addition of 0.125 μM (GAL 0.125 μM), 0.25 μM (GAL 0.25 μM), and 0.5 μM (GAL 0.5 μM) galectin-8 leads to approximately 2%, 43% and 74% decrease of TNFα levels respectively, illustrating that the effect of recombinant polypeptide galectin-8 on TNFα levels is dose dependent.

Figure 6:
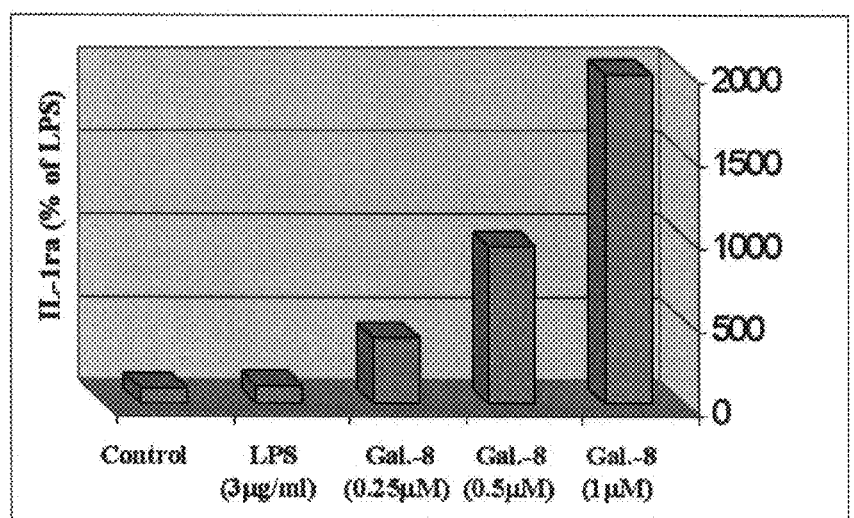

FIG. 6 is a bar graph depicting the effect of recombinant polypeptide galectin-8 (SEQ ID NO: 4) on IL-1ra levels found in media of synovial tissue culture medium supplemented with 3 μg/ml lipopolysaccharide (LPS). The bars compare IL-1ra levels (as a percentage of the IL-1ra level in LPS treated control) in media of synovial tissue cultures supplemented with increasing concentrations of galectin-8 (0.25 μM, 0.5 μM and 1 μM), following 48 hours of incubation. Data was collected using the quantified human immunoassay technique (see Example 5 for further details). The graph shows an increase of IL-1ra levels in media of synovial tissue cultures supplemented with recombinant polypeptide galectin-8 as compared with IL-1ra levels in medium of cells with no galectin-8 addition (LPS 3 μg/ml). Addition of 0.25 μM (GAL 0.25 μM), 0.5 μM (GAL 0.5 μM), and 1 μM (GAL 1 μM) galectin-8 leads to approximately 4-fold, 9-fold and 22-fold increase of IL-1ra levels respectively, verifying that the presence of LPS in the medium dramatically increases the effect of recombinant polypeptide galectin-8 on IL-1ra levels.

FIGS. 7a-d are bar graphs depicting the effect of recombinant polypeptide Galectin-8 var. 1 (SEQ ID NO: 6) on TNF-α levels in media of (FIG. 7a) NIH 3T3 Fibroblasts, (FIG. 7b) synovial fluid cells (SFCs), (FIG. 7c) human fibroblasts from osteoarthritic (OA) patients and (FIG. 7d) peripheral blood leucocutes (PBLs) from RA patients supplemented with 3 μg/ml lipopolysaccharide (LPS). Bars 11-18 compare TNFα levels in cell culture media supplemented with increasing concentrations of galectin-8 var. 1 (0, 50 125, 250, 500, 750, 1000, 2000 ng/ml), following 48 hours of incubation. Data was collected using the quantified human immunoassay technique (see Example 5 for further details). FIGS. 7b-d show a decrease in TNFα levels in media of the respective cultures supplemented with galectin-8 var. 1 (SEQ ID NO: 6). FIG. 7a shows that TNFα levels in media of 3T3 fibroblast cultures supplemented with galectin-8 var. 1 remain unaffected (negative control).

FIGS. 8a-d are bar graphs depicting the effect of recombinant polypeptide Galectin-8 var. 1 (SEQ ID NO: 6) on IL-1β1 levels in media of (FIG. 8a) 3T3 fibroblasts, (FIG. 8b) SFCs, (FIG. 8c) human fibroblasts from OA patients and (FIG. 8d) PBLs from RA patients supplemented with 3 μg/ml lipopolysaccharide (LPS). Bars 11-18 compare IL-1β levels in cell culture media supplemented with increasing concentrations of galectin-8 var. 1 (0, 50 125, 250, 500, 750, 1000, 2000 ng/ml), following 48 hours of incubation. Data was collected using the quantified human immunoassay technique (see Example 5 for further details). FIGS. 8b-d show a decrease in IL-1β levels in media of the respective cultures supplemented with galectin-8 var. 1 (SEQ ID NO: 6). FIG. 8a shows that IL-1β levels in media of 3T3 fibroblast cultures supplemented with galectin-8 var. 1 remain unaffected (negative control).

Figure 9A:
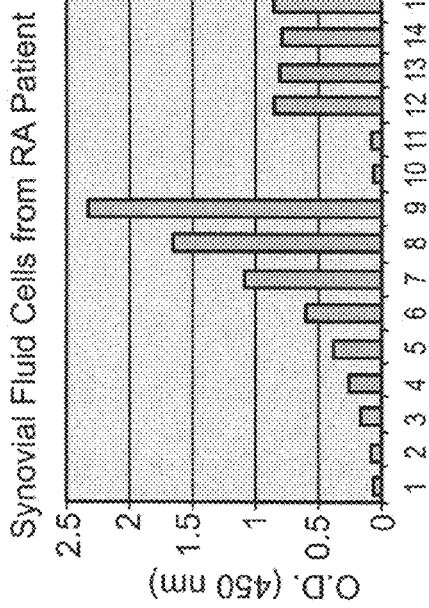
Figure 9B:
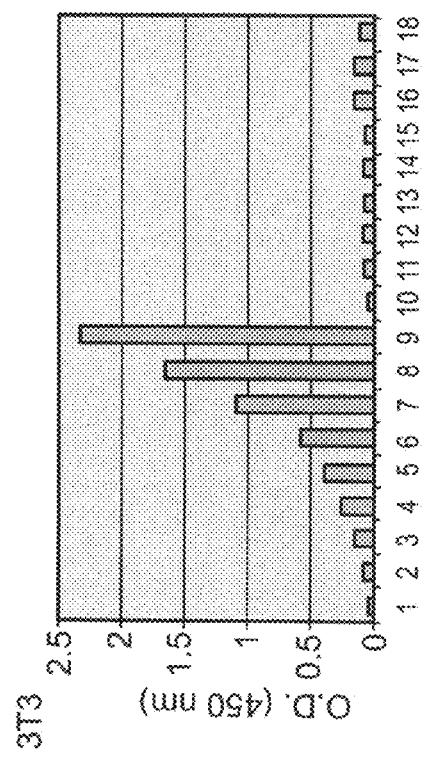
Figure 9C:
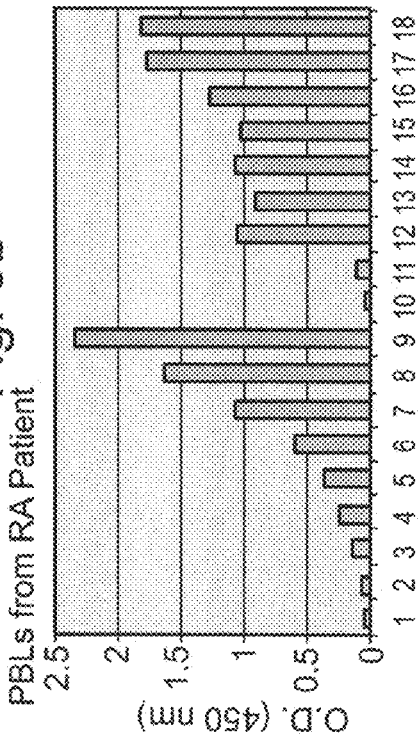
Figure 9D:
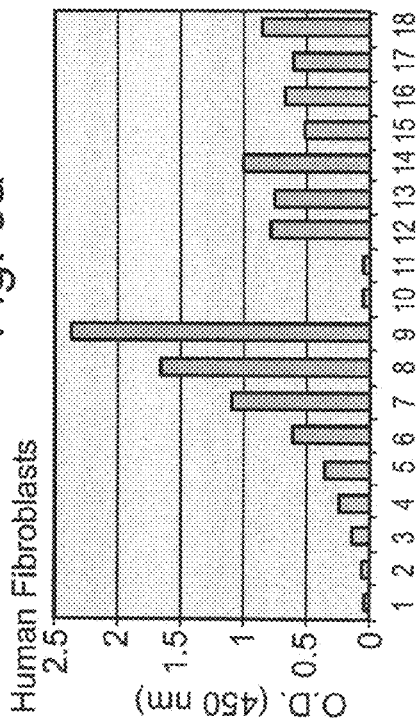

FIGS. 9a-d are bar graphs depicting the effect of recombinant polypeptide Galectin-8 var. 1 (SEQ ID NO: 6) on IL-1ra levels in media of (FIG. 9a) 3T3 fibroblasts (FIG. 9b) SFCs, (FIG. 9c) human fibroblasts from OA patients and (FIG. 9d) PBLs of RA patients supplemented with 3 μg/ml lipopolysaccharide (LPS). Bars 11-18 compare IL-1ra levels in cell culture media supplemented with increasing concentrations of galectin-8 var. 1 (0, 50 125, 250, 500, 750, 1000, 2000 ng/ml), following 48 hours of incubation. Data was collected using the quantified human immunoassay technique (see Example 5 for further details). FIGS. 9b-d show a decrease in IL-1ra levels in media of the respective cultures supplemented with galectin-8 var. 1 (SEQ ID NO: 6). FIG. 9a shows that IL-1ra levels in media of 3T3 fibroblast cultures supplemented with galectin-8 var. 1 remain unaffected (negative control).

Figure 10A:
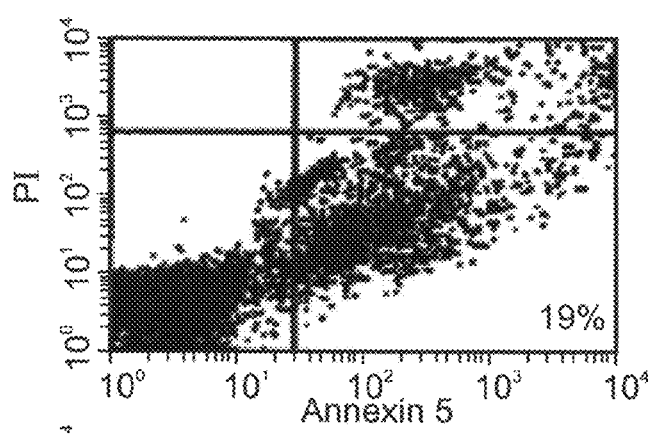
Figure 10B:
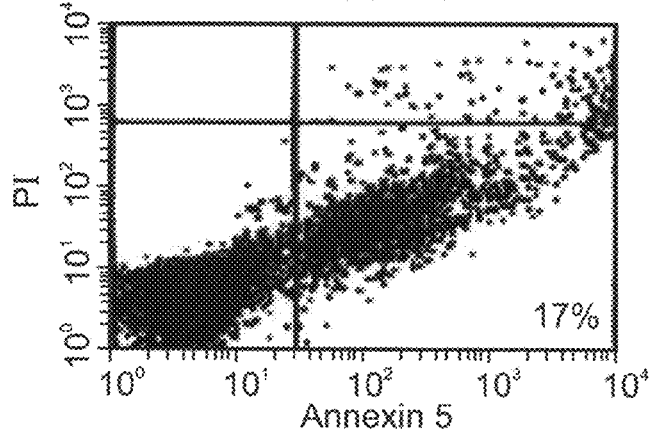
Figure 10C:
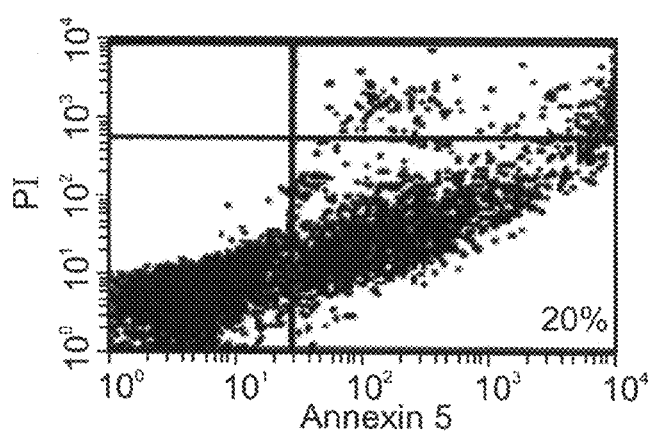
Figure 10D:
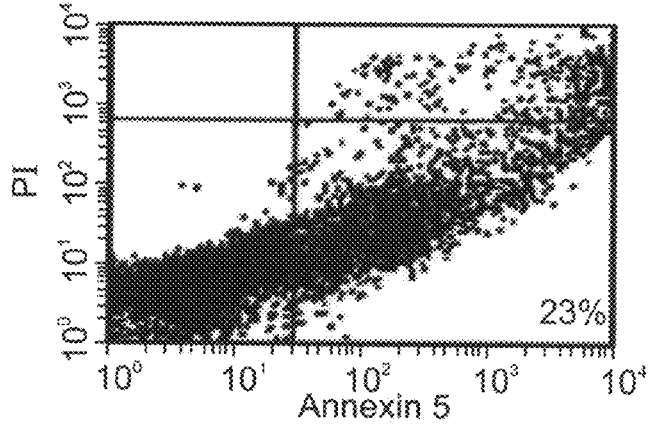
Figure 10E:
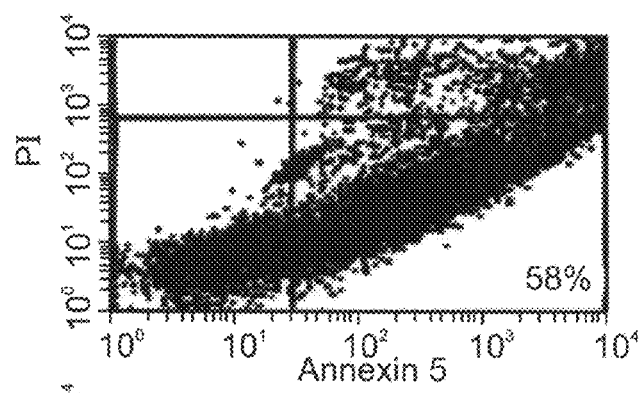
Figure 10F:
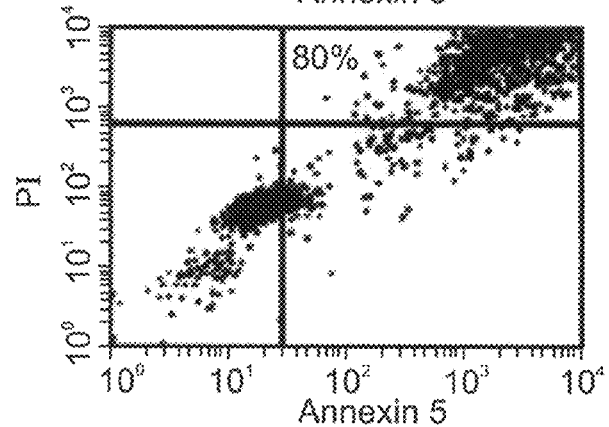

FIGS. 10a-f are scatter graphs depicting the effect of recombinant polypeptide galectin-8 (SEQ ID NO: 4) on the development of apoptosis in synovial fluid cells from RA patients. The plot graphs depict flow cytometric analysis of synovial fluid cells from RA patients incubated for 24 h with increasing concentrations of galectin-8 (FIGS. 10b-e), no galectin-8 (FIG. 10a) or doxorubicine (FIG. 10f) followed by staining with Phosphatidyl Serine Detection Kit (IOP-116F FITC-conjugated, IQ Products, The Netherlands) using the manufacturer instructions). Annexin $V^+/PI^+$ (green and red fluorescence) indicates necrotic cells, while annexin $V^+/PI^-$ (green fluorescence) indicates apoptotic cells. Live cells show little or no fluorescence. Data was collected using FACS analyzer (see Example 6 for further details). FIG. 10a is a plot depicting flow cytometric analysis of synovial fluid cells from RA patients incubated for 24 h with no galectin-8 addition. The plot shows red and green fluorescence of annexin V/PI stained cells, indicating the apoptotic state of untreated synovial fluid cells from RA patients after 24 h incubation. The plot shows 19% of the total cell population in the apoptotic area. FIG. 10b is a plot depicting flow cytometric analysis of synovial fluid cells from RA patients incubated for 24 h with 0.03 μM galectin-8 addition. The plot shows red and green fluorescence of annexin V/PI stained cells similar to that of the untreated control. The plot shows 17% of the total cells population in the apoptotic area, illustrating that addition of 0.03 μM galectin-8 does not change significantly the apoptosis development in synovial fluid cells from RA patients. FIG. 10c is a plot depicting flow cytometric analysis of synovial fluid cells from RA patients incubated for 24 h with 0.1 μM galectin-8. The plot shows red and green fluorescence of annexin V/PI stained cells similar to that of the untreated control. The plot shows 20% of the total cell population in the apoptotic area, illustrating that addition of 0.1 μM galectin-8 does not change significantly the apoptosis development in synovial fluid cells from RA patients. FIG. 10d is a plot depicting flow cytometric analysis of synovial fluid cells from RA patients incubated for 24 h with 0.3 μM galectin-8. The plot shows red and green fluorescence of annexin V/PI stained cells similar to that of the untreated control. The plot shows 23% of the total cell population in the apoptotic area, illustrating that addition of 0.3 μM galectin-8 slightly enhances apoptosis development in synovial fluid cells from RA patients. FIG. 10e is a plot depicting flow cytometric analysis of synovial fluid cells from RA patients incubated for 24 h with 1 μM galectin-8. The plot shows red and green fluorescence of annexin V/PI stained cells concentrated toward the apoptotic area compared with untreated control. The plot shows 58% of the total cell population in the apoptotic area, illustrating that addition of 1 μM galectin-8 resulted in a 3-fold increase in apoptosis development in synovial fluid cells from RA patients. FIG. 10f is a plot depicting flow cytometric analysis of synovial fluid cells from RA patients incubated for 24 h with doxorubicine (150 μg/ml). The plot shows red and green fluorescence of annexin V/PI stained cells. The plot shows 80% of the total cell population in the necrotic area, illustrating good quality of the experimental staining procedure.

FIGS. 11a-11n are a series of scatter graphs depicting the effect of increasing concentrations of recombinant polypeptides Galectin-8 var. 1 (SEQ ID NO: 6) and var. 2 (SEQ ID NO: 8) on the induction of apoptosis in human fibroblasts from OA patients. The plot graphs depict flow cytometric analysis of human fibroblast cells from OA patients incubated for 24 h with increasing concentrations of galectin-8 variant 1 (FIGS. 11b-11h) and galectin 8 variant 2 (FIGS. 11i-11n) followed by staining with Phosphatidyl Serine Detection Kit (IOP-116F FITC-conjugated, IQ Products, The Netherlands) using the manufacturer instructions. Events accumulating in the bottom left-hand quadrate of the flow cytometry image simulate surviving cells. Events accumulating at the top and bottom right-hand quadrates simulate apoptotic cells.

Data was collected using FACS analyzer (see Example 6 for further details). FIG. 11a is a plot depicting flow cytometric analysis of RPMI 1640 cells incubated for 24 h with no addition of galectin-8 variants. The plot shows 39.5% of the total cell population in the apoptotic area. FIG. 11b is a plot depicting flow cytometric analysis of human fibroblast cells from OA patients incubated for 24 h with 50 ng/ml galectin-8 variant 1. The plot shows 32.5% of the total cell population in the apoptotic area. FIG. 11c is a plot depicting flow cytometric analysis of human fibroblast cells from OA patients incubated for 24 h with 125 ng/ml galectin-8 variant 1. The plot shows 47.5% of the total cell population in the apoptotic area. FIG. 11d is a plot depicting flow cytometric analysis of human fibroblast cells from OA patients incubated for 24 h with 250 ng/ml galectin-8 variant 1. The plot shows 48.4% of the total cell population in the apoptotic area. FIG. 11e is a plot depicting flow cytometric analysis of human fibroblast cells from OA patients incubated for 24 h with 500 ng/ml galectin-8 variant 1. The plot shows 55.5% of the total cell population in the apoptotic area. FIG. 11f is a plot depicting flow cytometric analysis of human fibroblast cells from OA patients incubated for 24 h with 750 ng/ml galectin-8 variant 1. The plot shows 58.5% of the total cell population in the apoptotic area. FIG. 11g is a plot depicting flow cytometric analysis of human fibroblast cells from OA patients incubated for 24 h with 1000 ng/ml galectin-8 variant 1. The plot shows 77% of the total cell population in the apoptotic area. FIG. 11h is a plot depicting flow cytometric analysis of human fibroblast cells from OA patients incubated for 24 h with 2000 ng/ml galectin-8 variant 1. The plot shows 77% of the total cell population in the apoptotic area.

FIG. 11i is a plot depicting flow cytometric analysis of human fibroblast cells from OA patients incubated for 24 h with 125 ng/ml galectin-8 variant 2. The plot shows 52.2% of the total cell population in the apoptotic area. FIG. 11j is a plot depicting flow cytometric analysis of human fibroblast cells from OA patients incubated for 24 h with 250 ng/ml galectin-8 variant 2. The plot shows 50.8% of the total cell population in the apoptotic area. FIG. 11k is a plot depicting flow cytometric analysis of human fibroblast cells from OA patients incubated for 24 h with 500 ng/ml galectin-8 variant 2. The plot shows 62% of the total cell population in the apoptotic area. FIG. 11l is a plot depicting flow cytometric analysis of human fibroblast cells from OA patients incubated for 24 h with 750 ng/ml galectin-8 variant 2. The plot shows 59% of the total cell population in the apoptotic area. FIG. 11m is a plot depicting flow cytometric analysis of human fibroblast cells from OA patients incubated for 24 h with 1000 ng/ml galectin-8 variant 2. The plot shows 71.4% of the total cell population in the apoptotic area. FIG. 11n is a plot depicting flow cytometric analysis of human fibroblast cells from OA patients incubated for 24 h with 2000 ng/ml galectin-8 variant 2. The plot shows 77.4% of the total cell population in the apoptotic area.

FIGS. 12a-12p are a series of plot graphs depicting the effect of increasing concentrations of recombinant polypeptides Galectin-8 var. 1 (SEQ ID NO: 6) and var. 2 (SEQ ID NO: 8) on the induction of apoptosis in human synovial fluid cells from RA patients. The plot graphs depict flow cytometric analysis of human synovial fluid cells from RA patients incubated for 24 h with increasing concentrations of galectin-8 variant 1 (FIGS. 12c-12i) and galectin 8 variant 2 (FIGS. 12j-12p) followed by staining with Phosphatidyl Serine Detection Kit (IOP-116F FITC-conjugated, IQ Products, The Netherlands) using the manufacturer instructions). Events accumulating in the bottom left-hand quadrate of the flow cytometry image simulate surviving cells. Events accumulating at the top and bottom right-hand quadrates simulate apoptotic cells.

Data was collected using FACS analyzer (see Example 6 for further details). FIGS. 12a and 12b are plots depicting flow cytometric analysis of RPMI 1640 cells incubated for 24 h with no addition of galectin-8 variants. The plot shows 32.7% and 33.4% of the total cell population in the apoptotic area. FIG. 12c is a plot depicting flow cytometric analysis of human synovial fluid cells from RA patients incubated for 24 h with 50 ng/ml galectin-8 variant 1. FIG. 12d is a plot depicting flow cytometric analysis of human synovial fluid cells from RA patients incubated for 24 h with 125 ng/ml galectin-8 variant 1. FIG. 12e is a plot depicting flow cytometric analysis of human synovial fluid cells from RA patients incubated for 24 h with 250 ng/ml galectin-8 variant 1. FIG. 12f is a plot depicting flow cytometric analysis of human synovial fluid cells from RA patients incubated for 24 h with 500 ng/ml galectin-8 variant 1. FIG. 12g is a plot depicting flow cytometric analysis of human synovial fluid cells from RA patients incubated for 24 h with 750 ng/ml galectin-8 variant 1. FIG. 12h is a plot depicting flow cytometric analysis of human synovial fluid cells from RA patients incubated for 24 h with 1000 ng/ml galectin-8 variant 1. FIG. 12i is a plot depicting flow cytometric analysis of human synovial fluid cells from OA patients incubated for 24 h with 2000 ng/ml galectin-8 variant 1.

FIG. 12j is a plot depicting flow cytometric analysis of human synovial fluid cells from RA patients incubated for 24 h with 50 ng/ml galectin-8 variant 2. FIG. 12k is a plot depicting flow cytometric analysis of human synovial fluid cells from RA patients incubated for 24 h with 125 ng/ml galectin-8 variant 2. FIG. 12l is a plot depicting flow cytometric analysis of human synovial fluid cells from RA patients incubated for 24 h with 250 ng/ml galectin-8 variant 2. FIG. 12m is a plot depicting flow cytometric analysis of human synovial fluid cells from RA patients incubated for 24 h with 500 ng/ml galectin-8 variant 2. FIG. 12n is a plot depicting flow cytometric analysis of human synovial fluid cells from RA patients incubated for 24 h with 750 ng/ml galectin-8 variant 2. FIG. 12o is a plot depicting flow cytometric analysis of human synovial fluid cells from RA patients incubated for 24 h with 1000 ng/ml galectin-8 variant 2. FIG. 12p is a plot depicting flow cytometric analysis of human synovial fluid cells from OA patients incubated for 24 h with 2000 ng/ml galectin-8 variant 2.

FIGS. 13a-13p are a series of plot graphs depicting the effect of increasing concentrations of recombinant polypeptides Galectin-8 var. 1 (SEQ ID NO: 6) and var. 2 (SEQ ID NO: 8) on the induction of apoptosis in human peripheral blood leukocyte cells (PBLs) from RA patients. The plot graphs depict flow cytometric analysis of human PBLs from RA patients incubated for 24 h with increasing concentrations of galectin-8 variant 1 (FIGS. 13c-13i) and galectin 8 variant 2 (FIGS. 13j-13p) followed by staining with Phosphatidyl Serine Detection Kit (IOP-116F FITC-conjugated, IQ Products, The Netherlands) using the manufacturer instructions). Events accumulating in the bottom left-hand quadrate of the flow cytometry image simulate surviving cells. Events accumulating at the top and bottom right-hand quadrates simulate apoptotic cells.

Data was collected using FACS analyzer (see Example 6 for further details). FIGS. 13a and 13b are plots depicting flow cytometric analysis of RPMI 1640 cells incubated for 24 h with no addition of galectin-8 variants. The plot shows 1.7% and 2% of the total cell population in the apoptotic area. FIG. 13c is a plot depicting flow cytometric analysis of human PBLs from RA patients incubated for 24 h with 50 ng/ml galectin-8 variant 1. FIG. 13d is a plot depicting flow cytometric analysis of human PBLs from RA patients incubated for 24 h with 125 ng/ml galectin-8 variant 1. FIG. 13e is a plot depicting flow cytometric analysis of human PBLs from RA patients incubated for 24 h with 250 ng/ml galectin-8 variant 1. FIG. 13f is a plot depicting flow cytometric analysis of human PBLs from RA patients incubated for 24 h with 500 ng/ml galectin-8 variant 1. FIG. 13g is a plot depicting flow cytometric analysis of human PBLs from RA patients incubated for 24 h with 750 ng/ml galectin-8 variant 1. FIG. 13h is a plot depicting flow cytometric analysis of human PBLs from RA patients incubated for 24 h with 1000 ng/ml galectin-8 variant 1. FIG. 13i is a plot depicting flow cytometric analysis of human PBLs from RA patients incubated for 24 h with 2000 ng/ml galectin-8 variant 1.

FIG. 13j is a plot depicting flow cytometric analysis of human PBLs from RA patients incubated for 24 h with 50 ng/ml galectin-8 variant 2. FIG. 13k is a plot depicting flow cytometric analysis of human PBLs from RA patients incubated for 24 h with 125 ng/ml galectin-8 variant 2. FIG. 13l is a plot depicting flow cytometric analysis of human PBLs from RA patients incubated for 24 h with 250 ng/ml galectin-8 variant 2. FIG. 13m is a plot depicting flow cytometric analysis of human PBLs from RA patients incubated for 24 h with 500 ng/ml galectin-8 variant 2. FIG. 13n is a plot depicting flow cytometric analysis of human PBLs from RA patients incubated for 24 h with 750 ng/ml galectin-8 variant 2. FIG. 13o is a plot depicting flow cytometric analysis of human PBLs from RA patients incubated for 24 h with 1000 ng/ml galectin-8 variant 2. FIG. 13p is a plot depicting flow cytometric analysis of human PBLs from OA patients incubated for 24 h with 2000 ng/ml galectin-8 variant 2.

Figure 14:
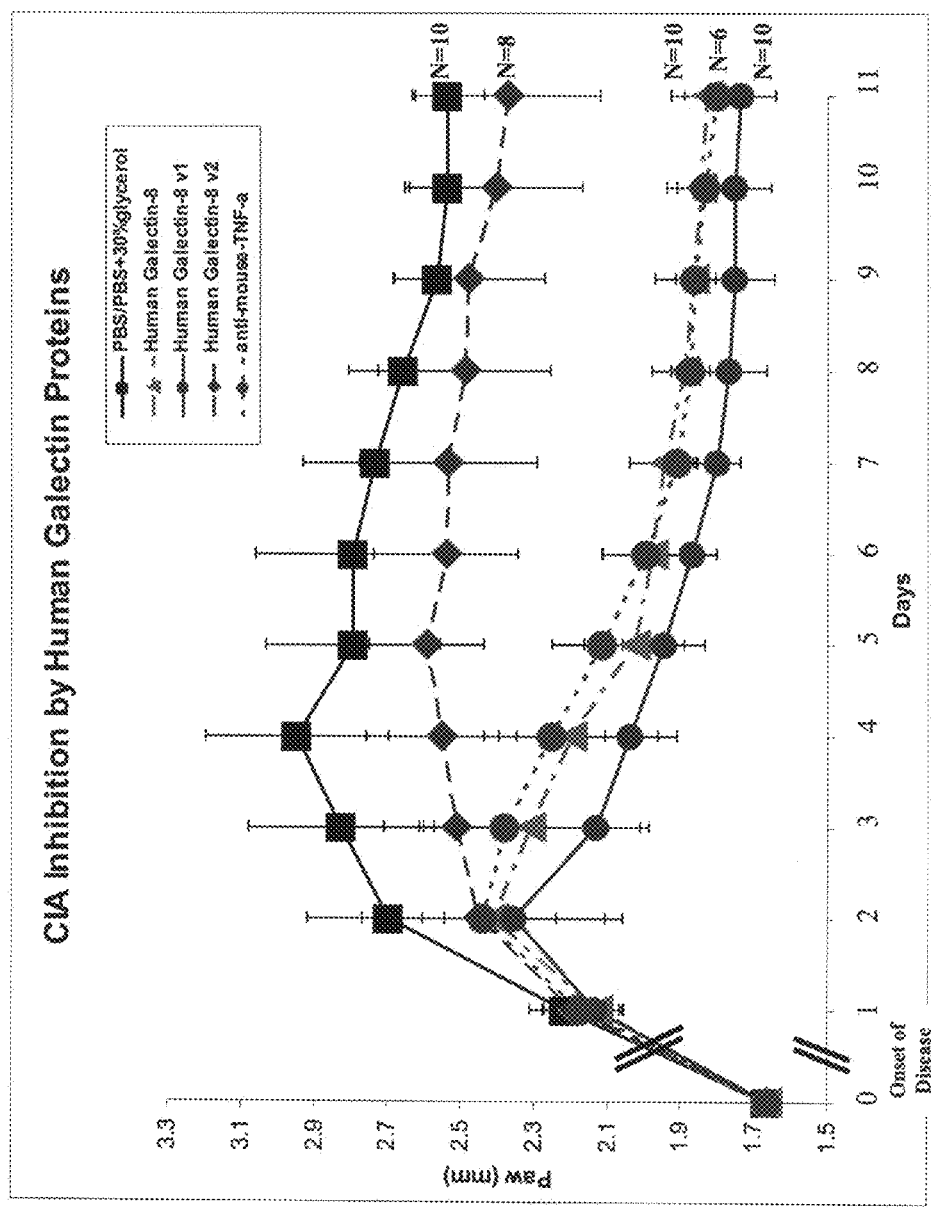

FIG. 14 is a line graph depicting the effect of human galectin recombinant peptides (SEQ ID NO: 4, 6 or 8) on collagen induced arthritis (CIA) in DBA/1 mice. Footpad thickness of the mice following systemic treatment immediately following disease onset was measured.

Black squares (negative control) represent the mean footpad thickness following systemic injection of PBS or PBS+ 30% glycerol (storing dilution solution of galectin proteins) in 10 mice. Dark red circles (positive control) represent the mean footpad thickness following systemic injection of TNFα mAb in 6 mice (100 µg antibody/mouse every day for 11 days). Red triangles represent the mean footpad thickness following systemic injection of human galectin-8 protein in 10 mice (100 µg antibody/mouse every day for 11 days). Blue circles represent the mean footpad thickness following systemic injection of human galectin-8 variant 1 peptide in 10 mice (100 µg antibody/mouse every day for 11 days). Purple diamonds circles represent the mean footpad thickness following systemic injection of human galectin-8 variant 2 peptide in 8 mice (100 µg antibody/mouse every day for 11 days).

Figure 15:
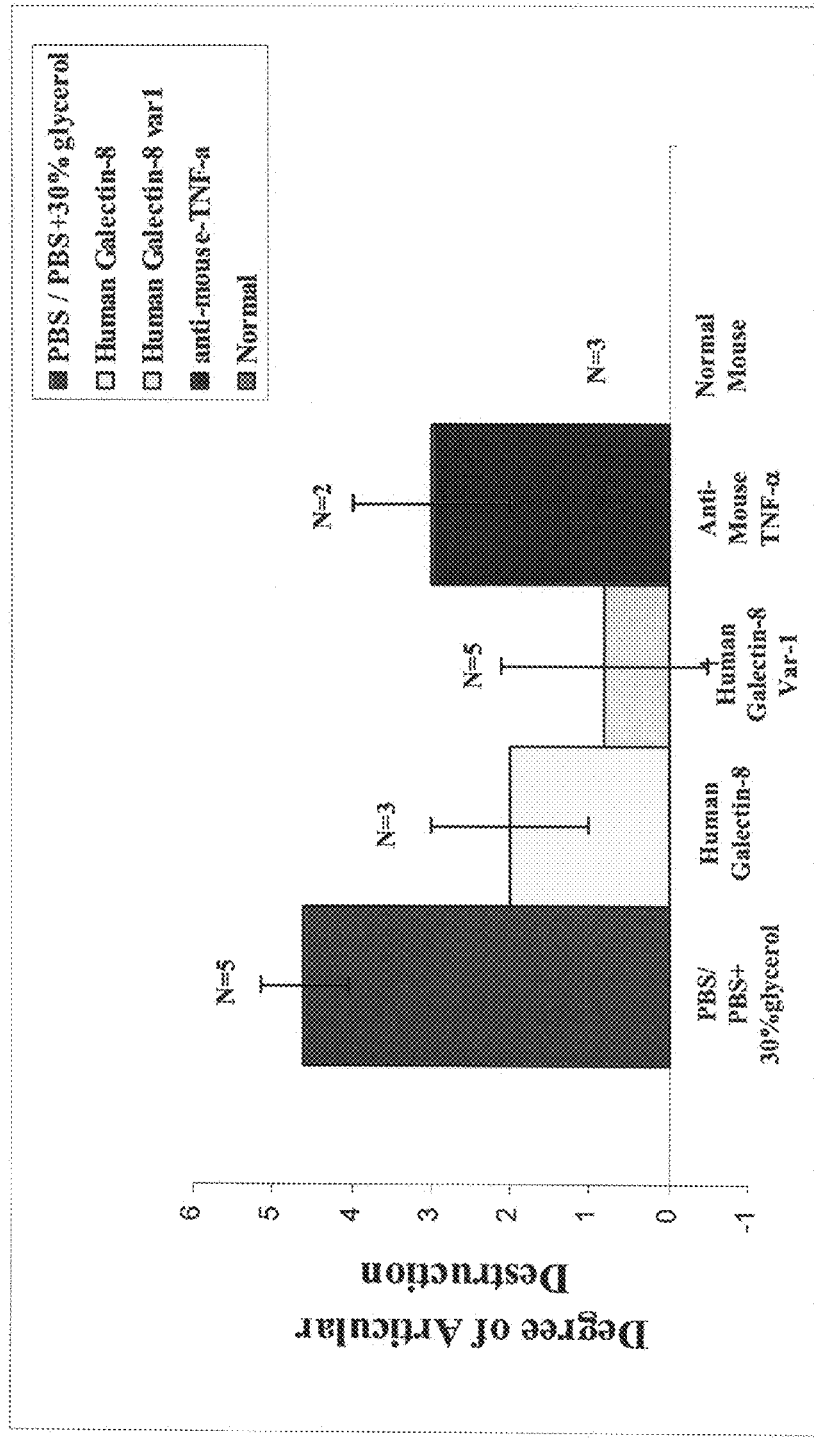

FIG. 15 is a bar graph depicting the degree of articular destruction following evaluation of the pathology analysis of the parameters described in Example 7 often observed in arthritic joints.

DESCRIPTION OF THE PREFERRED EMBODIMENTS

The present invention is of galectin-8 and novel variants thereof, which can be used in treatment, diagnosis and prognosis of chronic inflammatory diseases, such as rheumatoid arthritis (RA).

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

RA is a chronic inflammatory and destructive joint disease, which commonly leads to significant disability and a consequent reduction in quality of life [Gabriel, S. E., Rheum. Dis. Clin. North Am. 27:269, (2001)].

Drug therapy for RA rests on two principal approaches: symptomatic treatment with non-steroidal anti-inflammatory drugs (NSAIDs) and disease-modifying antirheumatic drugs (DMARDs). NSAIDs only interfere with a small segment of the inflammatory cascade, namely prostaglandin generation by cyclooxygenases (COXs), but do not interfere with the underlying immuno-inflammatory events and thus do not retard joint destruction. By contrast, DMARDs impede both the inflammatory and destructive processes of RA and as such, effective DMARDs treatment does not require additional symptomatic therapy [Smolen, J. S. and G. Steiner, Nat. Rev. Drug Discovery, 2:473 (2003)]. Although remission occurs in only 20-25% of DMARDs treated patients, continued DMARD treatment is advised since discontinuation of treatment significantly increases the risk of flares [ten Wolde, S. et al. Lancet 347:347, (1996)].

Among DMARDs presently used in RA therapy are drugs based on inhibition of pro-inflammatory cytokines. The pro-inflammatory role of cytokines, and the involvement of different cell types and their surface molecules in the pathogenesis of RA, provides the rationale for the development of highly specific therapeutics to target these molecules [Smolen, J. S. and G. Steiner, Nat. Rev. Drug Discovery, 2:473 (2003)].

Among such therapies are drugs which prevent interaction between pro-inflammatory cytokines, in particular Tumor Necrosis Factor (TNF) and Interleukin-1 (IL-1), and their receptors [Smolen, J. S. and G. Steiner, Nat. Rev. Drug Discovery, 2:473 (2003)].

The role of TNF in the pathogenesis of RA was elucidated in both experimental animals and in patients having RA [Feldmann, M. and Maini, R. N. Annu. Rev. Immunol. 19:163, (2001)]. Three drugs that block the activity of TNF have been approved: infliximab and adalimumab, which are antibodies against TNF, and etanercept which is a fusion protein of the TNF receptor II. All of these agents exhibited a therapeutic effect on RA patients, however, the response to treatment in over half the patients participating in clinical trials of these drugs were less than satisfactory. In addition, although remissions were rare in patients who responded to treatment, many side effects were prevalent in such patients [Smolen, J. S. and G. Steiner, Nat. Rev. Drug Discovery, 2:473 (2003)].

Interleukin 1 (IL-1) is another pro-inflammatory cytokine which has been implicated in the progression of RA. Binding of IL-1 to IL-1 receptor I (IL-1RI) allows the engagement of the IL-1R accessory protein (IL-1RacP) and subsequent cell signaling and activation. The natural inhibitor IL-1 receptor antagonist (IL-1ra), which belongs to the IL-1 family, competes with IL-1 for its receptor but does not allow engagement of IL-1RacP, thereby blocking activation of signal transduction mechanisms [Arend, W. P. et al., Annu. Rev. Immunol. 16:27 (1998)]. The importance of the role of IL-1ra in regulating the inflammatory response is exemplified by the occurrence of a destructive arthritis in IL-1ra-deficient animals [Horai, R. et al., J. Exp. Med. 191:313, (2000)]. Anakinra, a recombinant form of IL-1ra, is an RA drug which targets IL-1-blockage [Smolen, J. S. and G. Steiner, Nat. Rev. Drug Discovery, 2:473 (2003)].

The present inventors have previously uncovered that galectin-8 and variants thereof are capable of reducing the inflammatory response in human synovial tissue due to their ability to inhibit the release of the pro-inflammatory cytokines TNF-α and IL-1β, to increase the production of the anti-inflammatory cytokine IL-1ra and to induce apoptosis in synovial fluid cells (see PCT Appl. No. IL03/00960).

While reducing the present invention to practice, the present inventors have uncovered novel variants of galectin-8 (SEQ ID NOs: 15-16), which are capable of reducing the inflammatory response in human synovial tissue due to their ability to inhibit the release of the pro-inflammatory cytokines TNF-α and IL-1β, to increase the production of the anti-inflammatory cytokine IL-1ra and to induce apoptosis in synovial fluid cells.

Thus, according to one aspect of the present invention there is provided a method of detecting an inflammatory response in an individual.

As used herein the phrase "inflammatory response" refers to an immune response which results in inflammation, typically occurring as a result of injurious stimuli including infection, burns, trauma, neoplasia, autoimmune signals and exposure to chemicals, heat or cold or any other harmful stimulus. An inflammatory response according to the present invention refers to an acute phase response and a chronic inflammation.

As used herein the term "individual" refers to an individual, who may benefit from the present invention such as a mammal (e.g., canine, feline, ovine, porcine, equine, bovine, human), preferably a human individual.

The method of this aspect of the present invention is effected by identifying in a biological sample obtained from the individual, a transcription and/or translation product of a galectin-8 variant, wherein the presence of said transcription and/or translation product is indicative of an inflammatory response.

As used herein the phrase "transcription and/or translation product of a galectin-8 variant" refers to a gene expression product (i.e., RNA or protein) of a galectin-8 variant.

As used herein the term "variants" refers to splice variants and allelic variants of galectin-8.

The phrase "splice variant" refers to alternative forms of RNA transcribed from a galectin-8 gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

The phrase "allelic variant" refers to two or more alternative forms of a galectin-8 gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

Examples of transcriptional products of galectin-8 variants are set forth in SEQ ID NOs: 5, 7 and 15. Examples of translational products of galectin 8-variants (identified as part of the present study, further description of which is provided below) are set forth in SEQ ID NOs: 6, 8 and 16.

It will be appreciated that homologues of the sequences described hereinabove are also utilizable by the present invention.

Such homologues include for example a polynucleotide which encodes a polypeptide having a galectin-8 sequence which is devoid of the amino acid sequence coordinates 115-150 of SEQ ID NO: 4.

Preferably, the polynucleotide encodes a galectibe-8 variant polypeptide having an amino acid sequence coordinates 65-88 of SEQ ID NO: 16 (e.g., SEQ ID NO: 15 or 17).

According to one preferred embodiment of this aspect of the present invention, the polypeptide has an amino acid sequence at least 50%, at least 55%, at least 60%, at least 65%, at least 70%, at least 75%, at least 80%, at least 85%, at least 87%, at least 89%, at least 91%, at least 93%, at least 95% or more say 100% homologous to SEQ ID NO: 6, 8 or 16, as determined using BlastP software of the National Center of Biotechnology Information (NCBI) using default parameters.

According to another preferred embodiment of this aspect of the present invention the polynucleotide has a nucleic acid sequence at least 50%, at least 55%, at least 60%, at least 65%, at least 70%, at least 75%, at least 80%, at least 85%, at least 87%, at least 89%, at least 91%, at least 93%, at least 95% or more say 100% identical to SEQ ID NO: 5, 7 or 15, as determined using BlastN software of the National Center of Biotechnology Information (NCBI) using default parameters.

As used herein the phrase "biological sample" refers to a sample of tissue or fluid isolated from an individual, including, but not limited to, for example, plasma, serum, spinal fluid, lymph fluid, the external sections of the skin, respiratory, intestinal, and genitourinary tracts, tears, saliva, milk, blood cells, synovial cell fluid, tumors, organs such as synovial tissue and also samples of in vivo cell culture constituents (e.g., synovial fluid cells). Preferably, the biological sample is a synovial tissue or a synovial fluid.

Procedures for obtaining biological samples (i.e., biopsying) from individuals are well known in the art. Such procedures include, but are not limited to, bone biopsy, lymph node biopsy, pleural biopsy, skin biopsy, thyroid biopsy, CT-guided biopsy, joint biopsy, needle aspiration biopsy and breast biopsy. These and other procedures for obtaining tissue or fluid biopsies are described in details in http://www.healthatoz.com/healthatoz/Atoz/search.asp.

Specifically, a joint biopsy refers to a joint or synovial biopsy. In the procedure a sample of the joint lining or synovial membrane or fluid is taken. Briefly, the procedure is effected in a clinical facility by a surgeon. A number of approaches are available to perform this biopsy: such as through an incision in the joint; with a scope inserted in the joint; or, more typically, by the insertion of a sharp instrument through the skin. The sample can be taken from any joint; typically the examined joint is the knee. A sharp instrument (trocar) is pushed into the joint space. A needle with an attached syringe is inserted into the joint to withdraw fluid for laboratory analysis. The surgeon may instill analgesic compounds into the joint and along the needle track before the needle is withdrawn. The trocar and then the biopsy needle is inserted and specimens taken. After the specimen is taken, both the trocar and the biopsy needle are removed.

Regardless of the procedure employed, once the biological sample is obtained, the presence of the galectin-8 variant in the sample is determined.

As mentioned above, determination of the level of galectin-8 variant in the biological sample can be effected at the transcriptional level (i.e., mRNA) using an oligonucleotide probe, which is capable of specifically hybridizing to the variant sequence (e.g., SEQ ID Nos: 5, 7 or 15). Hybridization of oligonucleotide probes can be detected using a variety of methods known to those of skill in the art (e.g., colorimetric assays, amplification assays and the like).

The term "oligonucleotide" refers to a single stranded or double stranded oligomer or polymer of ribonucleic acid (RNA) or deoxyribonucleic acid (DNA) or mimetics thereof. This term includes oligonucleotides composed of naturally-occurring bases, sugars and covalent internucleoside linkages (e.g., backbone) as well as oligonucleotides having non-naturally-occurring portions which function similarly.

Oligonucleotides, which hybridize specifically with galectin-8 variants, are preferably those directed at unique nucleotide sequences, which are not shared by wild type galectin-8 (e.g., SEQ ID NO: 3). Thus, preferably avoided are nucleotide targets encompassed by the polynucleotide sequence encoding amino acid sequence coordinates 115-150 of SEQ ID NO: 4. Hence, oligonucleotides designed to hybridize to nucleotide coordinates 193-261 of SEQ ID NO: 5, can be used to detect the presence of galectin-8 RA1 variant (SEQ ID NO: 5) in the biological sample. Oligonucleotides designed to hybridize to exon junctions of SEQ ID NO: 7, such as those set forth in SEQ ID NOs: 9 and 10, can be used to detect the presence of galectin-8 RA2 variant (SEQ ID NO: 7) in the biological sample. Oligonucleotides designed to hybridize to exon junctions of SEQ ID NO: 15, such as those set forth in amino acids coordinates 193-264 of SEQ ID NO: 15 (SEQ ID NO: 17) can be used to detect the presence of galectin-8 RA1.1 variant (SEQ ID NO: 15) in the biological sample.

Oligonucleotides designed according to the teachings of the present invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988) and "Oligonucleotide Synthesis" Gait, M. J., ed. (1984) utilizing solid phase chemistry, e.g. cyanoethyl phosphoramidite followed by deprotection, desalting and purification by for example, an automated trityl-on method or HPLC.

The oligonucleotide of the present invention is of at least 17, at least 18, at least 19, at least 20, at least 22, at least 25, at least 30 or at least 40, bases specifically hybridizable with sequence alterations described hereinabove.

The oligonucleotides of the present invention may comprise heterocylic nucleosides consisting of purines and the pyrimidines bases, bonded in a 3' to 5' phosphodiester linkage.

Preferably used oligonucleotides are those modified in either backbone, internucleoside linkages or bases, as is broadly described hereinunder. Such modifications can oftentimes facilitate oligonucleotide uptake and resistivity to intracellular conditions.

Specific examples of preferred oligonucleotides useful according to this aspect of the present invention include oligonucleotides containing modified backbones or non-natural internucleoside linkages. Oligonucleotides having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other oligonucleotides which can be used according to the present invention, are those modified in both sugar and the internucleoside linkage, i.e., the backbone, of the nucleotide units are replaced with novel groups. The base units are maintained for complementation with the appropriate polynucleotide target. An example for such an oligonucleotide mimetic, includes peptide nucleic acid (PNA). A PNA oligonucleotide refers to an oligonucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082;

5,714,331; and 5,719,262, each of which is herein incorporated by reference. Other backbone modifications, which can be used in the present invention are disclosed in U.S. Pat. No. 6,303,374.

Oligonucleotides of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Such bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi Y S et al. (1993) Antisense Research and Applications, CRC Press, Boca Raton 276-278] and are presently preferred base substitutions, even more particularly when combined with 2'-O-methoxyethyl sugar modifications.

Hybridization of short nucleic acids (below 200 bp in length, e.g. 17-40 bp in length) can be effected by the following hybridization protocols depending on the desired stringency: (i) hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 1-1.5° C. below the $T_m$, final wash solution of 3 M TMACl, 0.01 M sodium phosphate (pH 6.8), 1 mM EDTA (pH 7.6), 0.5% SDS at 1-1.5° C. below the $T_m$; (ii) hybridization solution of 6×SSC and 0.1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 2-2.5° C. below the $T_m$, final wash solution of 3 M TMACl, 0.01 M sodium phosphate (pH 6.8), 1 mM EDTA (pH 7.6), 0.5% SDS at 1-1.5° C. below the $T_m$, final wash solution of 6×SSC, and final wash at 22° C.; (iii) hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 37° C., final wash solution of 6×SSC and final wash at 22° C.

Determination of hybridization complexes is well known in the art and may be achieved by any one of several approaches. These approaches are generally based on the detection of a label or marker, such as any radioactive, fluorescent, biological or enzymatic tags or labels of standard use in the art. A label can be conjugated to either the oligonucleotide probes or the nucleic acids derived from the biological sample (target).

For example, oligonucleotides of the present invention can be labeled subsequent to synthesis, by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent. Alternatively, when fluorescently-labeled oligonucleotide probes are used, fluorescein, lissamine, phycoerythrin, rhodamine (Perkin Elmer Cetus), Cy2, Cy3, Cy3.5, Cy5, Cy5.5, Cy7, FluorX (Amersham) and others [e.g., Kricka et al. (1992), Academic Press San Diego, Calif] can be attached to the oligonucleotides.

It will be appreciated that a variety of controls may be usefully employed to improve accuracy of hybridization assays. For instance, samples may be hybridized to an irrelevant probe and treated with RNAse A prior to hybridization, to assess false hybridization.

Polymerase chain reaction (PCR)-based methods (e.g., RT-PCR) may also be used to identify galectin-8 variants. For PCR-based methods a pair of oligonucleotides is used, which is specifically hybridizable with the galectin-8 polynucleotide sequences described hereinabove in an opposite orientation so as to direct exponential amplification of a portion thereof (including the hereinabove described sequence alteration) in a nucleic acid amplification reaction. For example, an oligonucleotide pair of primers which can hybridize with the galectin-8 variants of the present invention is set forth in SEQ ID NOs: 1 and 2; SEQ ID NOs: 11 and 12; SEQ ID NOs: 13 and 14 (see Example 1, 2 and 8 of the Examples section). Such primers will amplify galectin 8 polynucleotides and variants which share flanking sequences (i.e., SEQ ID NOs. 3, 5 7 and 15). In such case identification of each variant can be effected by, for example, sequencing or fine electrophoresis.

The polymerase chain reaction and other nucleic acid amplification reactions are well known in the art and require no further description herein. The pair of oligonucleotides according to this aspect of the present invention are preferably selected to have compatible melting temperatures (Tm), e.g., melting temperatures which differ by less than that 7° C., preferably less than 5° C., more preferably less than 4° C., most preferably less than 3° C., ideally between 3° C. and 0° C.

Methods for detecting minor polynucleotide sequence alterations (e.g., such as insertion of T at nucleotide coordinate 494 of SEQ ID NO: 7) can also be used according to this aspect of the present invention. Such methods include, but are not limited to, single-strand conformational polymorphism (SSCP), denaturing gradient-gel electrophoresis (DGGE), heteroduplex analysis (HET), chemical cleavage analysis (CCM), ribonuclease cleavage (RNAase), and direct sequencing of the target. More direct methods of mutation analysis include but are not limited to allele-specific amplification (ASA), oligonucleotide ligation assay (OLA), primer extension, artificial introduction of restriction sites (AIRS), allele-specific oligonucleotide hybridization (ASO), and variations of these procedures [Cotton, R. G. H. (1993) Mutat Res, 285, 125-144; Forrest, S. (1995) Nat Genet, 10, 375-376; Orita, M., (1989) Proc Natl Acad Sci U.S.A., 86, 2766-2770; Myers, R. M. (1985) Nature, 313, 495-498; Keen, J. (1991) Trends Genet, 7, 5. 10; Cotton, R. G. H. (1988) Proc Natl Acad Sci U.S.A., 85, 4397-4401; Myers, R. M. (1985) Science, 230, 1242-1246; Sanger (1977) Proc Natl Acad Sci U.S.A., 74, 5463-5467; Newton, C. R. (1989) Nucl Acids Res, 17, 2503-2516; Landegren, U. (1988) Science, 241, 1077-1080; Sokolov, B. P. (1990) Nucl Acids Res, 18, 3671].

Detection of galectin-8 variants can also be effected at the protein level. A number of protein detection methods are known in the art. Examples include, but are not limited to, chromatography and electrophoretic methods which are preferably used to detect polypeptides mainly based on molecular weight variation and immunodetection assays such as ELISA and western blot analysis, immunohistochemistry and the like, which may be effected using antibodies specific to the galectin-8 variants of the present invention.

Preferably used are antibodies, which specifically interact with the galectin-8 variants of the present invention. Such antibodies are directed to, for example, the unique sequence portions of the polypeptide variants of the present invention (e.g., amino acid coordinates 65-87 of SEQ ID NO: 6, amino acid coordinates 162-170 of SEQ ID NO: 8 or amino acid coordinates 65-88 of SEQ ID NO: 16 such as set forth in SEQ ID NO: 18) or to unique sequences, which bridge the galectin-8 common portion and the unique sequence regions. Specific peptides chosen for antibody generation are preferably selected immunogenic (i.e., capable of stimulating an antibody response). Parameters for testing peptide immunogenicity are well known in the art including, but not limited to, foreginess, molecular size, chemical composition and heterogeneity and susceptibility to antigen processing and presentation. Various sequence analysis software applications are known in the art, which provide an immunogenicity index according to, for example, the Jameson-Wolf algorithm. Examples include, but are not limited to, Sciprot (available from www.asiaonline.net.hk/~twcbio/DOCS/1/scPrtein.htm) and Macvector (available from www.accelrys.com/products/macvector/) as well as the widely utilized GCG package (Genetics Computer Group, Wisconsin).

The term "antibody" as used in this invention includes whole antibody molecules as well as functional fragments thereof, such as Fab, F(ab')$_2$, and Fv that are capable of binding with antigenic portions of the target polypeptide. These functional antibody fragments constitute preferred embodiments of the present invention, and are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule as described in, for example, U.S. Pat. No. 4,946,778.

Methods of generating such antibody fragments are well known in the art. (See for example, Harlow and Lane, Antibodies: A Laboratory Manual, Cold Spring Harbor Laboratory, New York, 1988, incorporated herein by reference).

Purification of serum immunoglobulin antibodies (polyclonal antisera) or reactive portions thereof can be accomplished by a variety of methods known to those of skill in the art including, precipitation by ammonium sulfate or sodium sulfate followed by dialysis against saline, ion exchange chromatography, affinity or immunoaffinity chromatography as well as gel filtration, zone electrophoresis, etc. (see Goding in, Monoclonal Antibodies: Principles and Practice, 2nd ed., pp. 104-126, 1986, Orlando, Fla., Academic Press). Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains. Additional classes include IgD, IgE, IgA, IgM and related proteins.

Methods for the generation and selection of monoclonal antibodies are well known in the art, as summarized for example in reviews such as Tramontano and Schloeder, Methods in Enzymology 178, 551-568, 1989. A recombinant galectin-8 polypeptide of the present invention may be used to generate antibodies in vitro. More preferably, the recombinant galectin-8 of the present invention is used to elicit antibodies in vivo. In general, a suitable host animal is immunized with the recombinant Galectin-8 of the present invention. Advantageously, the animal host used is a mouse of an inbred strain. Animals are typically immunized with a mixture comprising a solution of the recombinant Galectin-8 of the present invention in a physiologically acceptable vehicle, and any suitable adjuvant, which achieves an enhanced immune response to the immunogen. By way of example, the primary immunization conveniently may be accomplished with a mixture of a solution of the recombinant Galectin-8 of the present invention and Freund's complete adjuvant, said mixture being prepared in the form of a water in oil emulsion. Typically the immunization will be administered to the animals intramuscularly, intradermally, subcutaneously, intraperitoneally, into the footpads, or by any appropriate route of administration. The immunization schedule of the immunogen may be adapted as required, but customarily involves several subsequent or secondary immunizations using a milder adjuvant such as Freund's incomplete adjuvant. Antibody titers and specificity of binding to the Galectin-8 can be determined during the immunization schedule by any convenient method including by way of example radioimmunoassay, or enzyme linked immunosorbant assay, which is known as the ELISA assay. When suitable antibody titers are achieved, antibody-producing lymphocytes from the immunized animals are obtained, and these are cultured, selected and cloned, as is known in the art. Typically, lymphocytes may be obtained in large numbers from the spleens of immunized animals, but they may also be retrieved from the circulation, the lymph nodes or other lymphoid organs. Lymphocytes are then fused with any suitable myeloma cell line, to yield hybridomas, as is well known in the art. Alternatively, lymphocytes may also be stimulated to grow in culture, and may be immortalized by methods known in the art including the exposure of these lymphocytes to a virus, a chemical or a nucleic acid such as an oncogene, according to established protocols. After fusion, the hybridomas are cultured under suitable culture conditions, for example in multi-well plates, and the culture supernatants are screened to identify cultures containing antibodies that recognize the hapten of choice.

Hybridomas that secrete antibodies that recognize the recombinant Galectin-8 of the present invention are cloned by limiting dilution and expanded, under appropriate culture conditions. Monoclonal antibodies are purified and characterized in terms of immunoglobulin type and binding affinity.

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, in U.S. Pat. Nos. 4,036,945 and 4,331,647, and references contained therein, which patents are hereby incorporated by reference in their entirety (see also Porter, R. R., Biochem. J., 73: 119-126, 1959). Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al. (Proc. Nat'l Acad. Sci. USA 69:2659-62, 1972). Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, all of which are hereby incorporated, by reference, in entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick and Fry Methods, 2: 106-10, 1991).

Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues, which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321: 522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source, which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human monoclonal antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

A number of diseases and conditions, which involve an inflammatory response can be diagnosed using the methodology described hereinabove. Examples of such diseases and conditions are summarized infra.

Inflammatory diseases—Include, but are not limited to, chronic inflammatory diseases and acute inflammatory diseases.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2): 49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49;77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12):2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Cancerous Diseases

Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

Diagnostic agents of the present invention (e.g., oligonucleotide and antibodies, described above) can be packaged in a diagnostic kit. Such diagnostic kits can include an antibody (e.g., labeled) of the present invention in one container and a solid phase for attaching multiple biological samples packaged in a second container as well as imaging reagent in a third container (e.g., secondary labeled antibody) with appropriate buffers and preservatives and used for diagnosis.

As mentioned hereinabove and further illustrated in the Examples section which follows, galectin 8 is capable of reducing inflammatory response, probably due to its ability to inhibit the release of the pro-inflammatory cytokines TNF-α and IL-1β, to increase the production of the anti-inflammatory cytokine IL-1ra and to induce apoptosis in synovial fluid cells, rendering it a valuable tools in a number of therapeutic applications.

Thus, according to another aspect of the present invention there is provided a method of reducing an inflammatory response in an individual.

The method is effected by providing to the individual a galectin-8 polypeptide or a galectin 8 variant (as described above) or derivative thereof to thereby reduce the inflammatory response in the individual.

As used herein the term "galectin-8 polypeptide" refers to human galectin-8 (SEQ ID NOs: 3 and 4, AF74000) and orthologues, such as encoded by the polynucleotide sequences listed in Table 1 below.

TABLE 1

| Gene Name | Species | GenBank accession number |
|---|---|---|
| LGALS8 | Homo sapiens | AAF19370 |
| LGALS8 | Homo sapiens | O00214 |
| dJ670F13.2.2 | Homo sapiens | CAC15946 |
| PCTA-1 | Homo sapiens | JC6147 |
| Unknown | Homo sapiens | AAH16486 |
| PCTA-1 | Homo sapiens | AAB51605 |
| Po66-CBP | Homo sapiens | AAD45403 |
| LGALS8 | Homo sapiens | NP_006490 |
| GAL-8 | Homo sapiens | CAA62904 |
| dJ670F13.2 | Homo sapiens | CAC15947 |
| LGALS8 | Homo sapiens | AAL77076 |
| Coca galectin-8II | Homo sapiens | AAK16736 |
| LGALS8 | Rattus norvegicus | NP_446314 |
| LGALS8 | Mus musculus | NP_061374 |
| Unknown | Mus musculus | BAC35918 |
| LGALS8 | Homo sapiens | AAK69827 |
| Xgalectin-VIIIa | Xenopus laevis | BAC55887 |

As used herein a "galectin-8 derivative" refers to a fragment of the galectin-8 polypeptides and variants and polypeptides having mutations such as deletion, insertion or substitution of one or more amino acids, either naturally occurring or man-induced either randomly or in a targeted fashion, as long as its anti-inflammatory is maintained (i.e., functional equivalent). Screening of such galectin 8 derivatives can be effected as described in Examples 5, 6 and 7 of the Examples section below.

Provision of the above-described polypeptide can be effected by administering it to the individual.

The term "polypeptide" as used herein encompasses native polypeptides (either degradation products, synthetically synthesized polypeptides or recombinant polypeptides) and peptidomimetics (typically, synthetically synthesized polypeptides), as well as peptoids and semipeptoids which are polypeptide analogs, which may have, for example, modifications rendering the polypeptides more stable while in a body or more capable of penetrating into cells. Such modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Polypeptide bonds (—CO—NH—) within the polypeptide may be substituted, for example, by N-methylated bonds (—N(CH3)-CO—), ester bonds (—C(R)H—C—O—O—C(R)—N—), ketomethylen bonds (—CO—CH2—), α-aza bonds (—NH—N(R)—CO—), wherein R is any alkyl, e.g., methyl, carba bonds (—CH2-NH—), hydroxyethylene bonds (—CH(OH)—CH2—), thioamide bonds (—CS—NH—), olefinic double bonds (—CH=CH—), retro amide bonds (—NH—CO—), polypeptide derivatives (—N(R)—

CH2-CO—), wherein R is the "normal" side chain, naturally presented on the carbon atom.

These modifications can occur at any of the bonds along the polypeptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the polypeptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 2 and 3 below list naturally occurring amino acids (Table 2) and non-conventional or modified amino acids (Table 3) which can be used with the present invention.

TABLE 2

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 3

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cyclododeclglycine | Ncdod |

TABLE 3-continued

| Non-conventional amino acid | Code | Non-conventional amino acid | Code |
|---|---|---|---|
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dmnval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenylethylamino) cyclopropane | Nmbc | | |

Since the present polypeptides are preferably utilized in therapeutics which require the polypeptides to be in a soluble form, the polypeptides of the present invention preferably include one or more non-natural or natural polar amino acids, including but not limited to serine and threonine which are capable of increasing polypeptide solubility due to their hydroxyl-containing side chain.

The polypeptides of the present invention are preferably utilized in a linear form, although it will be appreciated that in cases where cyclicization does not severely interfere with polypeptide characteristics, cyclic forms of the polypeptide can also be utilized.

The polypeptides of present invention can be biochemically synthesized such as by using standard solid phase techniques. These methods include exclusive solid phase synthesis, partial solid phase synthesis methods, fragment condensation, classical solution synthesis. These methods are preferably used when the polypeptide is relatively short (i.e., 10 kDa) and/or when it cannot be produced by recombinant techniques (i.e., not encoded by a nucleic acid sequence) and therefore involves different chemistry.

Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Synthetic polypeptides can be purified by preparative high performance liquid chromatography [Creighton T. (1983) Proteins, structures and molecular principles. WH Freeman and Co. N.Y.] and the composition of which can be confirmed via amino acid sequencing.

Recombinant techniques are preferably used to generate the polypeptides of the present invention since these techniques are better suited for generation of relatively long polypeptides (e.g., longer than 20 amino acids) and large amounts thereof. Such recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp. 421-463.

To produce a polypeptide of the present invention using recombinant technology, a polynucleotide encoding a polypeptide of the present invention is ligated into a nucleic acid expression vector, which includes the polynucleotide sequence under the transcriptional control of a promoter sequence suitable for directing constitutive tissue specific or inducible transcription in the host cells Polynucleotide sequences, which can be used to express the polypeptides of the present invention, include isolated polynucleotides which encode the polynucleotides described above (see Table 1, and SEQ ID NOs: 3, 5, 7 and 15) and homologues thereof (described above).

The phrase "an isolated polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

Such isolated polynucleotides of the present invention can be verified using hybridization assays. Thus, the isolated polynucleotides of the present invention are preferably hybridizable with SEQ ID NO: 5, 7 or 15 under moderate to stringent hybridization conditions.

Moderate to stringent hybridization conditions are characterized by a hybridization solution such as containing 10% dextrane sulfate, 1 M NaCl, 1% SDS and $5 \times 10^6$ cpm $^{32}$P labeled probe, at 65° C., with a final wash solution of 0.2× SSC and 0.1% SDS and final wash at 65° C. and whereas moderate hybridization is effected using a hybridization solution containing 10% dextrane sulfate, 1 M NaCl, 1% SDS and $5 \times 10^6$ cpm $^{32}$P labeled probe, at 65° C., with a final wash solution of 1×SSC and 0.1% SDS and final wash at 50° C.

As mentioned hereinabove, polynucleotide sequences of the present invention are inserted into expression vectors to enable expression of the recombinant polypeptide. The expression vector of the present invention includes additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals). Detailed description of expression vectors is provided hereinbelow.

A variety of prokaryotic or eukaryotic cells can be used as host-expression systems to express the polypeptides of the present invention. These include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence. Mammalian expression systems can also be used to express the polypeptide of the present invention. Bacterial systems are preferably used to produce recombinant polypeptides since they enable a high production volume at low cost.

In bacterial systems, a number of expression vectors can be advantageously selected depending upon the use intended for the polypeptide expressed. For example, when large quantities of polypeptide are desired, vectors that direct the expression of high levels of the protein product, possibly as a fusion with a hydrophobic signal sequence, which directs the expressed product into the periplasm of the bacteria or the culture medium where the protein product is readily purified may be desired. Certain fusion protein engineered with a specific cleavage site to aid in recovery of the polypeptide may also be desirable. Such vectors adaptable to such manipulation include, but are not limited to, the pET series of *E. coli* expression vectors [Studier et al., Methods in Enzymol. 185:60-89 (1990)].

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

In cases where plant expression vectors are used, the expression of the polypeptide coding sequence can be driven by a number of promoters. For example, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] can be used. Alternatively, plant promoters can be used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-

565 (1986)]. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp. 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Various methods can be used to introduce the expression vector of the present invention into the host cell system. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant polypeptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

Depending on the vector and host system used for production, resultant polypeptides of the present invention may either remain within the recombinant cell, secreted into the fermentation medium, secreted into a space between two cellular membranes, such as the periplasmic space in *E. coli*; or retained on the outer surface of a cell or viral membrane.

Following a predetermined time in culture, recovery of the recombinant polypeptide is effected.

The phrase "recovering the recombinant polypeptide" used herein refers to collecting the whole fermentation medium containing the polypeptide and need not imply additional steps of separation or purification.

Thus, polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

To facilitate recovery, the expressed coding sequence can be engineered to encode the polypeptide of the present invention and fused cleavable moiety. Such a fusion protein can be designed so that the polypeptide can be readily isolated by affinity chromatography; e.g., by immobilization on a column specific for the cleavable moiety. Where a cleavage site is engineered between the polypeptide and the cleavable moiety, the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

The polypeptide of the present invention is preferably retrieved in "substantially pure" form.

As used herein, the phrase "substantially pure" refers to a purity that allows for the effective use of the protein in the applications described herein.

In addition to being synthesizable in host cells, the polypeptide of the present invention can also be synthesized using in vitro expression systems. These methods are well known in the art and the components of the system are commercially available.

Production of galectin-8 polypeptides using recombinant DNA technology is illustrated in Example 2 and 8 of the Examples section which follows.

Once the recombinant polypeptide is synthesized and purified, its therapeutic efficacy can be assayed either in vivo or in vitro. For example the recombinant polypeptides can be administered to collagen-induced arthritic (CIA) mice in vivo. CIA is a well accepted animal model of human RA. The decrease in footpad swelling can then be measured (as in Example 7 of the Examples section which follows). Alternatively, or additionally the recombinant polypeptides may be added to cultures of arthritic synovial cells and the amount of apoptosis can be measured by FACS analysis—(as in Example 6). Example 5 of the Example section below demonstrates the assaying recombinant galectin peptides by their ability to decrease cytokines such as IL-1β, IL-1ra and TNF-1α. in an in vitro cell culture system.

The polypeptides of the present invention can be provided to the individual per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the polypeptide or antibody preparation, which is accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the preparation in a local rather than systemic manner, for example, via injection of the preparation directly into a specific region of a patient's body. Thus, for example, the preparation may be directly injected into a joint of an RA patient by intra-articular administration.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

It will be appreciated that the polypeptides of the present invention can also be expressed from a nucleic acid construct administered to the individual employing any suitable mode of administration, described hereinabove (i.e., in-vivo gene therapy). Systemic administration of various factors (e.g., cytotoxic T lymphocyte antigen CTLA4 and CIA) to RA patients was successfully achieved using viral delivery systems such as described below.

Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

Thus, for example, polynucleotides encoding galectin-8 and variants thereof can be introduced into a population of synovial cells. Briefly, synovial tissue is removed by joint surgery and cells are expanded and infected in vitro prior to being re-introduced into the joint space. Synovial tissue may be removed several days later by joint arthoplasty for expression analysis. This approach was successfully used in a clinical trial for RA involving nine patients, aiming to express IL-1Ra. Evidence for IL-1Ra expression was provided both at the transcriptional level and at the protein level. This study of local ex vivo retroviral gene therapy of RA demonstrated that safe and effective transgene expression can be achieved [Evans (1999) Arthritis Rheum 42:S170]. It will be appreciated that using this approach it is also possible to infect the cells with agents, which promote expression of endogenous galectin-8 (e.g., transcription factors or polynucleotide sequences which manipulate the promoter region of galectin-8 to achieve enhanced expression).

Regardless of the procedure used for administration, to enable cellular expression, galectin-8 polypeptides of the present invention are ligated into nucleic acid expression constructs under the transcriptional control of a promoter sequence suitable for directing constitutive, tissue specific or inducible transcription in the cells.

Constitutive promoters suitable for use with the present invention include sequences which are functional (i.e., capable of directing transcription) under most environmental conditions and most types of cells such as the cytomegalovirus (CMV) and Rous sarcoma virus (RSV).

Tissue specific promoters suitable for use with the present invention include sequences which are functional in specific cell population, example include, but are not limited to promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166). Inducible promoters suitable for use with the present invention include for example the tetracycline-inducible promoter (Srour, M. A., et al., 2003. Thromb. Haemost. 90: 398-405).

As mentioned above, the expression vector of the present invention includes additional sequences which render this vector suitable for replication and integration in prokaryotes, eukaryotes, or preferably both (e.g., shuttle vectors). Typical cloning vectors contain transcription and translation initiation sequences (e.g., promoters, enhances) and transcription and translation terminators (e.g., polyadenylation signals).

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

Polyadenylation sequences can also be added to the expression vector in order to increase the translation efficiency of a polypeptide expressed from the expression vector of the present invention. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of the present invention can further include additional polynucleotide sequences that allow, for example, the translation of several proteins from a single mRNA such as an internal ribosome entry site (IRES) and sequences for genomic integration of the promoter-chimeric polypeptide.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can also be used by the present invention. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I).

Recombinant viral vectors are useful for in vivo expression of the polypeptides of the present invention since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells. Intra-articular injection of adeno associated virus (AAV) encoding soluble TNF receptor I was recently shown to significantly decrease synovial hyperplasia, and cartilage and bone destruction, in TNF-α transgenic mice [Zhang Hum Gene Ther 2000, 11:2431-2442].

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

It will be appreciated that the polypeptides of the present invention can be provided to the individual with additional active agents to achieve an improved therapeutic effect as compared to treatment with each agent by itself. In such therapy, measures (e.g., dosing and selection of the complementary agent) are taken to adverse side effects which may be associated with combination therapies.

Administration of such combination therapy can be simultaneous, such as in a single capsule having a fixed ration of these active agents, or in multiple capsules for each agent.

Thus, for example, the polypeptides of the present invention can be administered along with nonsteroidal anti-inflammatory drugs (NSAID), disease-modifying antirheumatic drugs (DMARDS), corticosteroids, analgesics, Fibromyalgia medications, chemotherapeutic agents and others such as listed in Table 4, below.

TABLE 4

| DRUG | BRAND NAME(S) |
|---|---|
| DMARDs—disease-modifying antirheumatic drugs | |
| Auranofin (oral gold) | Ridaura |
| Azathioprine | Imuran |
| Cyclophosphamide | Cytoxan |
| Cyclosporine | Neoral, Sandimmune |

TABLE 4-continued

| DRUG | BRAND NAME(S) |
|---|---|
| Gold sodium thiomalate (injectable gold) | Myochrysine |
| Hydroxychloro-quine sulfate | Plaquenil |
| Leflunomide | Arava |
| Methotrexate | Rheumatrex, Trexall |
| Minocycline | Minocin |
| Penicillamine | Cuprimine, Depen |
| Sulfasalazine | Azulfidine, Azulfidine EN-Tabs |
| Biological response modifiers | |
| Etanercept | Enbrel |
| Infliximab | Remicade |
| Anakinra | Kineret |
| Adalimumab | Humira |
| NSAIDs—nonsteroidal anti-inflammatory drugs | |
| Traditional NSAIDs | |
| Diclofenac potassium | Cataflam |
| Diclofenac sodium | Voltaren, Voltaren XR |
| Diclofenac sodium with misoprostol | Arthrotec |
| Diflunisal | Dolobid |
| Etodolac | Lodine, Lodine XL |
| Fenoprofen calcium | Nalfon |
| Flurbiprofen | Ansaid |
| Ibuprofen | Motrin, Advil, Motrin IB, Nuprin |
| Indomethacin | Indocin Indocin SR |
| Ketoprofen | Orudis Oruvail Actron, Orudis, KT |
| Meclofenamate sodium | Meclomen |
| Mefenamic acid | Ponstel |
| Meloxicam | Mobic |
| Nabumetone | Relafen |
| Naproxen | Naprosyn, Naprelan |
| Naproxen sodium | Anaprox, Aleve |
| Oxaprozin | Daypro |
| Piroxicam | Feldene |
| Sulindac | Clinoril |
| Tolmetin sodium | Tolectin |
| COX-2 Inhibitors | |
| Celecoxib | Celebrex |
| Rofecoxib | Vioxx |
| Valdecoxib | Bextra |
| Salicylates | |
| Acetylated Salicylates | |
| Aspirin | Anacin, Ascriptin, Bayer, Bufferin, Ecotrin, Excedrin tablets |
| Nonacetylated Salicylates | |
| Choline and magnesium salicylates | CMT, Tricosal, Trilisate |
| Choline salicylate (liquid only) | Arthropan |
| Magnesium salicylate | Magan, Mobidin, Mobogesic, Arthritab, Bayer Select, Doan's Pill |
| Salsalate | Amigesic, Anaflex 750, Disalcid, Marthritic, Mono-Gesic, Salflex, Salsitab |
| Sodium salicylate (Available as generic only) | |
| Corticosteroids | |
| Cortisone | Cortone, Acetate |
| Dexamethasone | Decadron, Hexadrol |
| Hydrocortisone | Cortef, Hydrocortone |
| Methylprednisolone | Medrol |
| Prednisolone | Prelone |
| Prednisolone sodium phosphate (liquid only) | Pediapred |
| Prednisone | Deltasone, Orasone, Prednicen- |
| Analgesics | |
| Acetaminophen | Anacin (aspirin-free), Excedrin caplets, Panadol, Tylenol, Tylenol Arthritis |
| Acetaminophen with codeine | Phenaphen with Codeine, Tylenol with Codeine |
| Hydrocodone with acetaminophen | Dolacet, Hydrocet, Lorcet, Lortab, Vicodin |

TABLE 4-continued

| DRUG | BRAND NAME(S) |
|---|---|
| Morphine sulfate | Avinza, Oramorph |
| Oxycodone | OxyContin, Roxicodone, OxyFAST, OxyIR (liquid) |
| Oxycodone with acetaminophen | Percocet |
| Propoxyphene hydrochloride | Darvon, PP-Cap |
| Propoxyphene with acetaminophen | Darvocet |
| Tramadol | Ultram |
| Tramadol with acetaminophen | Ultracet |
| Fibromyalgia medications | |
| Antidepressants - tricyclics | |
| Amitriptyline hydrochloride | Elavil, Endep |
| Doxepin | Adapin, Sinequan |
| Nortriptyline | Aventyl, Pamelor |
| Antidepressants - SSRIs | |
| Citalopram | Celexa |
| Fluoxetine | Prozac |
| Paroxetine | Paxil |
| Sertraline | Zoloft |
| Antidepressants -other | |
| Bupropion | Wellbutrin, Zyban Wellbutrin SR |
| Trazodone | Desyrel, Trazon, Trialodine |
| Venlafaxine | Effexor |
| Nefazodone | Serzone |
| Benzodiazepines | |
| Temazepam | Restoril |
| Aprazolam | Xanax |
| Clonazepam | Klonopin |
| Lorazepam | Ativan |
| Other | |
| Cyclobenzaprine | Cycloflex, Flexeril |
| Carisoprodol | Soma |
| Gabapentin | Neurontin |
| Modafinil | Provigil |
| Orphenadrine | Norflex |
| Tizanidine | Zanaflex |
| Zaleplon | Sonata |
| Gout medications | |
| Allopurinol | Lopurin, Zyloprim |
| Colchicine (Only available as generic) | |
| Probenecid | Benemid, Probalan |
| Probenecid and Colchicine | ColBenemid, Col-Probenecid, Proben-C |
| Sulfinpyrazone | Anturane |
| Osteoporosis medications | |
| Alendronate | Fosamax |
| Calcitonin (nasal spray) | Miacalcin |
| Conjugated estrogens | Premphase, Prempro, Activella, Premarin |
| Esterified Estrogen | Estratab, Estrace, Menest |
| Raloxifene hydrochloride | Evista |
| Risedronate sodium | Actonel |
| Teriparatide | Forteo |

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions; illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "A Practical Guide to Molecular Cloning" Perbal, B., (1984) and Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Cloning of Galectin-8 and Galectin-8 Variants

Materials and Methods
A. Cloning of Galectin-8
RNA Preparation: Total RNA of mononuclear cells (MNC) derived from synovial fluids of RA patients was extracted using the Qiagen RNeasy kit (Qiagen, USA).
RT-PCR: 1 µg of the extracted RNA was reverse transcribed, and PCR-amplified using M-MuLV reverse transcriptase (first strand cDNA synthesis kit, Pharmacia) and Taq DNA polymerase (2.5 units) (Gibco-BRL). The reactions were carried out in a DNA thermal cycler 480 (Perkin Elmer Cetus) in a final volume of 50 µl using oligonucleotide primers complementary to a translated region of human galectin-8: [sense primer 5'-AA GAATTCGCCGCCACCATGATGTTGTCCTTAAAC-3' (SEQ ID NO:1), antisense primer 5'-AA TCTAGACTACCAGCTCCTTACTTC-3' (SEQ ID NO:2)].
The above described reaction mixture was subjected to an amplification program of 1 min at 94° C., 1 min at 60° C. and 2 min at 72° C. for 30 cycles.
Purification of PCR Product, Sequence Analysis and Cloning of Human Galectin-8: PCR products were gel-purified and sequenced (ABI PRISM 310, PerkinElmer, Wellesley, Mass.). The PCR product corresponding to galectin-8 encoding sequence (SEQ ID NO:3) (GenBank Accession No: AF074000), [see also Hadari, Y. R., et al., Trends In Glycoscience and Glycobiology 9, 103-112, 1997] was subcloned into pGEM vector (Promega) to generate pGEM-galectin-8 and purified with a commercial kit (Promega). The plasmid, pGEM-galectin-8 was used as a template for a second PCR reaction generating galectin-8 PCR product (SEQ ID NO: 3).

B. Cloning of Human Galectin Variants 1 and 2
RNA Preparation: For cloning of human galectin variant 1 and 2 cDNAs, the total synovial fluid cell population of RA patients undergoing joint aspiration was isolated. RNA was isolated with a commercial kit (Promega, Madison, Wis., USA).
RT-PCR: 1 µg of the extracted RNA was reverse transcribed and amplified, as described in Example 1, but reactions were carried out in PTC-100™ Programmable Therminal Controller (MJ Research, Watertown, Mass.). PCR products of 2464 bp, 657 bp and 669 bp were gel-purified and sequenced (ABI PRISM 310, PerkinElmer, Wellesley, Mass.).
The reactions resulted in the wild-type galectin-8 PCR product (SEQ ID NO: 3), RA variant 1 (SEQ ID NO:5) and RA variant 2 (SEQ ID NO:7) products.
Cloning of Human Galectin Variant 1.1
RNA Preparation: Total RNA was prepared as in the cloning of human galectin variants 1 and 2,
RT-PCR: RNA was reverse transcribed and amplified as in the cloning of human galectin variants 1 and 2 herein above except the following oligonucleotides complementary to a translated region of human galectin-8 were used:
a sense primer 5'CC TCTAGAATGATGTTGTCCTTAAAC-3' (SEQ ID NO:13); and an antisense primer 5'-GC CATATGCTACCAGCTCCTTACTTC-3' (SEQ ID NO: 14),
The reactions resulted in the galectin-8 variant 1.1 PCR product (SEQ ID NO: 15), Example 2

Expressing Recombinant Galectin-8 Molecules in *Escherichia Coli*

Materials and Methods
In order to express recombinant-galectin-8 molecules (r-galectin-8 (SEQ ID NO: 4), r-galectin-8 variant 1 (SEQ ID NO: 6), r-galectin-8 variant 2 (SEQ ID NO: 8)) in *E. coli*, the following primers were used to amplify the entire coding sequence of human galectin-8 using the cloned cDNA in pGEM vector (Promega) as a template:

```
sense primer:
                                        (SEQ ID NO: 11)
5'ACTCTAGAGCCGCCACCATGATGTTGTCCTTAAAC-3', antisense primer:
                                        (SEQ ID NO: 12)
5'-CCATATTCCTACCAGCTCCTTACTTC-3'.
```

In order to express recombinant-galectin-8 variant 1.1 molecule (SEQ ID NO:16) the following primers were used:

```
sense primer:
5'CCTCTAGAATGATGTTGTCCTTAAAC-3';     (SEQ ID NO: 13)

antisense primer:
5'-GCCATATGCTACCAGCTCCTTACTTC-3',    (SEQ ID NO: 14)
```

(The Xba I and Nde I restriction sites, respectively, in the above primers are underlined).
The PCR products were digested by Xba I and Nde I, gel-purified and ligated into a pET-3a expression plasmid (Novagen) in the pLyaS bacterial host. Sequencing of the expression plasmids were carried out to ensure proper, in frame, ligation of the insert. The plasmids were purified with a commercial kit (Promega) and then introduced into a pLyaS bacterial host. The transformed bacteria were cultured in 0.5 liter of LB medium until the absorbance at 600 nm was 0.5. The expression of the plasmids was induced with 5 mM isopropyl-1-thio-β-D-galactopy-ranoside for 4 h.

Isolation of the recombinant galectin proteins: Bacterial pellets were isolated by centrifugation, resuspended in 30 ml buffer I (phosphate-buffered saline containing 4 mM β-mercaptoethanol, 2 mM EDTA, 10 μg/ml soybean trypsin inhibitor, 2 mM benzamidine and 1 mM phenylmethylsulfonyl fluoride, pH 7.5), lysed by sonication and centrifuged (38,000×g at 4° C. for 45 min). 30 ml of the soluble extract were passed over 5 ml of Lactosyl-Sepharose. Unbound proteins were eluted with buffer I, while the lectin was subsequently eluted with buffer I containing 100 mM lactose.

The production of recombinant galectin-8 polypeptide together with the variants was verified by their size after running of the protein samples on 7.5% acrylamide-SDS gel and Coomassie blue staining (see FIG. 2).

The biological activity of the galectins under study was assayed by measuring their ability to agglutinate formaldehyde-fixed trypsin treated rabbit erythrocytes. Rabbit erythrocytes were trypsin-treated according to Lis and Sharon (20). Hemagglutinating activity and inhibition of hemagglutination by different sugars were assayed by serial dilution in microtiter U-shaped plates as described (20). The minimal inhibitory concentration of different sugars was measured by incubating serial diluted sugars with galectin-8 variants (0.5 μM) in a final volume of 50 μl for 20 minutes, following which 50 μl of a 4% suspension of packed rabbit erythrocytes in PBS was added for 30 minutes at 22° C.

Example 3

Flow Cytometry Analysis of Galectin-8 Expression on Synovial Fluid Cells and PBLs and Recombinant Galectin-8 Binding to Such Cells Materials and Methods Peripheral white blood cells and the total cell population from synovial fluids of arthritic patients were isolated (approximately $10^7$ cells) on a Ficoll gradient (Robbins Scientific Corporation, Sunngvale, Calif., USA) and analyzed by flow cytometry using anti-galectin-8 polyclonal antibody (generated in rabbits according to prior art protocols).

Specific binding of anti-galectin-8 was performed by the incubation of cells for 20 minutes on ice in a binding calcium buffer containing a saturating concentration of anti-galectin-8. Thereafter, a second incubation with a goat-anti-rat conjugated to fluorescein isothiocyanate (FITC) was effected. After incubation, the cells were pelleted, and analyzed in FACS analyzer (Beckton Dickinson, San Jose, Calif.). Following the initial analysis, recombinant galectin-8 (as prepared in Example 1) (1 μM) was added to both the synovial fluid cells and the PBLs to verify that recombinant galectin-8 may be detected by immunostaining with anti-galectin-8 polyclonal antibody.

Results

Endogenic expression of galectin molecules on synovial fluid cells of all tested samples were found (representative results are shown in FIG. 3A). Conversely, no galectin-8 expression was found on the surface of PBLs from all parallel blood samples, as indicated by their negative immunostaining with anti-galectin-8 polyclonal antibody (representative results are shown in FIG. 3B). Recombinant galectin-8 was detected in both the PBLs and the synovial fluid cells (see FIGS. 3A and 3B orange curve).

Example 4

RT-PCR Analysis of Galectin-8 Variants Expression in Cells Derived from Synovial Fluids and PBLs from Different Arthritic Patients Materials and Methods RNA was extracted from $2\times10^6$ synovial fluid cells and peripheral blood leukocytes (PBLs) of arthritic patients using a commercial kit (Promega, Madison, Wis., USA). 1 μg of the extracted RNA was reverse transcribed and amplified, as described in Example 1 with oligo dT primers. The PCR products were analyzed on an agarose gel and sequenced.

Results

Both novel isoforms of human galectins were discovered in the synovial fluid cells of arthritic patients by RT-PCR of galectin transcripts as confirmed by sequencing. Approximate band sizes of the transcripts were 2464, 657 bp and 669 bp. The 2464 bp product was the sequence encoding galectin-8 (GenBank Accession No: AF074000), while the other two transcripts designated galectin RA variant 1 [(SEQ ID NO:5 and SEQ ID NO:6) nucleotide and amino acid sequences, respectively] and galectin RA variant 2 [(SEQ ID NO:7 and SEQ ID NO:8) nucleotide and amino acid sequences, respectively] were both the galectin-8 variants of the present invention. The three products were detected in the synovial fluid cells of all arthritic patients whose RT-PCR products were sequenced. When the same RT-PCR reaction was performed on the peripheral blood, only the transcript of 2464 bp of galectin-8 was detected, suggesting local expression of the new galectin variants in synovial fluids of RA patients.

TABLE 5

| Diagnosis | Number of Patients |
| --- | --- |
| Rheumatoid Arthritis | 15 |
| Psoriatic Arthritis | 1 |
| Spondyloarthropathy | 2 |
| Gout | 1 |
| Osteoarthritis | 4 |
| Osteoarthritis with CPPD | 2 |
| Miscellaneous non-specified arthritis | 14 |

Example 5

The Anti-Inflammatory Effect of Recombinant Human Galectin-8 Peptides on Human Fibroblasts from OA Patients, Synovial Fluid Cells and PBLs from RA and Other Arthritic Patients The aim of the study was to examine the ability of human galectin-8 variants 1 and 2 to reduce the inflammatory response in vitro of human fibroblasts from synovial tissue of inflammatory cells derived from joint fluids of arthritic patients and of PBLs from the same patients.

Materials and Methods

Specimen Selection and Culture Conditions: Synovial tissues were obtained from patients undergoing total knee or hip replacement for osteoarthritis (OA). Within 2 hours of removal, synovial tissues were cut into small pieces, of a few millimeters in diameter. Synovial fibroblasts were cultured in 2 ml RPMI 1640 supplemented with 2 mM L-glutamine, 100 U/ml penicillin and 100 µg/ml streptomycin sulphate (Biological Industries).

Inflammatory cells and PBLs derived from joints of rheumatoid arthritic (RA) patients were cultured individually [RPMI-1640 (Sigma, Israel)]. The murine fibroblast line, NIH 3T3, was used as a control. The recombinant galectin-8 peptide (r-galectin-8) was added to the culture medium of the synovial fibroblasts at a concentration of 0.125 µM, 0.25 µM, 0.5 µM and 1 µM) together with lipopolysaccharide (LPS, 3 µg/ml). The recombinant galectin-8 peptide variants (r-galectin-8 variant 1 and r-galectin-8 variant 2) were added to all the culture mediums in the following concentrations: 50 ng/ml, 125 ng/ml, 250 ng/ml, 500 ng/ml, 750 ng/ml, 1 µg/ml and 2 µg/ml together with lipopolysaccharide (LPS, 3 µg/ml). Following 48 hours of incubation (37° C., 5% $CO_2$), the measurement of IL-1β, TNF-α and IL-1ra production was performed in supernatants by quantitative sandwich enzyme immunoassay technique (R&D Systems, Inc., USA). Detection limits were 1 pg/ml to 14 pg/ml. IL-1ra production was tested with and without the addition of lipopolysaccharide (LPS, 3 µg/ml) to the culture media.

Cell Viability and Toxicity Determination: Cell viability in the presence of galectin-8 was determined in human synovial cultures by trypan blue exclusion test and by the tetrazolium salt XTT assay (19).

Statistical Analysis: Statistical significance (determination of p values) was determined by analysis of variance and by Student's t-test. P values of less then 0.05 were considered statistically significant.

Results

Human recombinant galectin-8 (0.25 µM, 0.5 µM and 1 µM) inhibited TNF-α and IL-1β release in the media of human synovial tissue as compared with LPS treated control in a dose dependent fashion (FIGS. 4 and 5).

Human galectin-8 (0.25 µM, 0.5 µM and 1 µM) increased the IL-1ra production in the media of human synovial tissue as compared with untreated control in a dose dependent fashion (FIG. 6).

Human galectin-8 variants 1 and 2 significantly and dose-dependently inhibited TNF-α and IL-1β release in the media of human synovial fibroblasts, inflammatory cells derived from joints of arthritic patients and PBLs of the same patients (representative results of human galectin-8 variant 1 are shown in FIGS. 7B-D and 8B-D). No effect was seen in the control NIH 3T3 cells (FIGS. 7A and 8A). In addition, human galectin-8 variants 1 and 2 significantly and dose-dependently increased the IL-1ra production in the media of human fibroblasts from synovial tissue, of inflammatory cells derived from joints of arthritic patients and of PBLs of same patients (representative results of human galectin-8 variant 1 are shown in FIGS. 9B-D). No effect was seen in the control NIH 3T3 cells (FIG. 9A).

Conclusion

TNF and IL-1 are mediators of the innate immune system, and they enhance inflammation and destruction in various ways, mostly through effects on endothelial cells, synovial fibroblasts, osteoclasts and cartilage. The inhibition of these cytokines was shown to ameliorate the symptoms and joint destruction of RA [Pope R. M., Nat. Rev. Immun., 2:527, (2002)]. Published studies confirmed that the long term use of a several biological agents targeting TNFα give rise to sustained improvements in symptoms and signs of rheumatoid disease and, furthermore, that TNFα blockade protects joints from structural damage [Taylor P. C., Curr. Pharm. Des., 9:1095 (2003)]. IL-1-receptor antagonist (IL-1Ra) is produced in healthy subjects and helps to protect against the adverse effects associated with IL-1 overexpression. Administration of IL-1Ra (Anakinra) for RA patients was shown ameliorate inflammatory conditions [Louie S. G., et al., Am. J. Health Syst. Pharm., 60:346, (2003); Wendling, D. and Jorgensen C., Rev. Med. Interne., 23:1006 (2002)].

Galectin-8 and the Galectin 8 variants 1 and 2 all combine the anti-inflammatory effect of three factors. They act to reduce the production of TNFα and IL-1β while increasing the production of IL-1ra. Each of these effects was shown to reduce inflammatory response in arthritic patients and therefore galectin-8 that combines these effects presents a new advantageous therapeutic agent for various forms of arthritis.

Example 6

The Apoptotic Effect of Human Galectin-8 and Human Galectin-8 Variants on Human Fibroblasts from OA Patient, Synovial Fluid Cells and PBLs from RA and Other Arthritic Patients The ability of human galectin-8 recombinant polypeptide (r-galectin-8—SEQ ID NO: 4), and the galectin-8 variants 1 and 2 (r-galectin-8 variant 1—SEQ ID NO: 6 and r-galectin-8 variant 2—SEQ ID NO: 8) to induce programmed cell death in human fibroblasts cultured from synovial tissue of OA patient, joint fluid inflammatory cells and PBLs of arthritic patients was analyzed.

Materials and Methods

The assay was performed by Phosphatidyl Serine Detection Kit (IOP-116F FITC-conjugated, IQ Products, The Netherlands) using the manufacturer instructions. Human fibroblast cells from OA patients, synovial fluid cells and PBLs from RA and other arthritic patients were incubated with increasing concentrations of galectin-8 variants 1 and 2 (50-2000 ng/ml). Specific binding of annexin V was performed by the incubation of cells for 20 minutes on ice in a binding calcium buffer containing a saturating concentration of annexin V-fluorescein isothiocyanate (FITC) and propdium iodide (PI). After incubation, the cells were pelleted, and analyzed in FACS analyzer (Beckton Dickinson, San Jose, Calif.). Annexin $V^+/PI^+$ cells were defined as necrotic, while annexin $V^+/PI^-$ cells were defined as apoptotic. The percent of the apoptotic cells of the total cells was determined.

Results

A. Apoptosis Induction by Galectin-8

Galectin-8 (0.03 µM, 0.1 µM, 0.3 µM and 1 µM) induced apoptotic effects in human synovial fluid cells as compared with treatments with serum free medium (negative control) and doxorubicine (positive control) in a dose dependent fashion (FIGS. 10a-f).

B. Apoptosis Induction by Galectin-8 Variants 1 and 2

Increasing concentrations of human galectin-8 variants 1 and 2 added to human synovial fibroblasts from OA patients gradually increased the percentage of apoptotic cells (representative results are shown in FIG. 11a-n). More sensitive to apoptotic effect of human galectin-8 variants 1 and 2 were inflammatory cells from joints and PBLs of arthritic patients in which significant and maximal apoptotic effect (approximately 100%) was determined even at the lowest concentration (50 ng/ml) of human galectin-8 proteins (representative results are shown in FIGS. 12a-p and FIGS. 13a-p).

Conclusions

Several studies have shown the possibility that some of the pathophysiological consequences of RA may be explained by inadequate apoptosis [Rabinovich G. A., Mem Inst Oswaldo Cruz., 95:225, (2000)]. RA synovial tissue contains few neutrophils, whereas macrophages, synovial fibroblasts and lymphocytes are abundant. Insufficient apoptosis possibly contributes to the increased numbers of synovial fibroblasts and chronic inflammatory cells in RA joints [Pope R. M., Nat. Rev. Immun., 2:527, (2002)]. Galectin-1 was shown to gain therapeutic advantage in the disease when used to induce apoptosis in rheumatoid joints [Rabinovich G. A., Mem Inst Oswaldo Cruz., 95:225, (2000)].

By inducing apoptosis in human synovial fluid cells, galectin-8 and galectin-8 variants 1 and 2, were shown to have therapeutic effects on chronic inflammatory cells.

These findings also show that the pro-apoptotic effects of human galectin-8 variants 1 and 2 are able to discriminate between cells involved in pathological functions (synovial fluid inflammatory cells) and cells engaged in normal physiological activities in joints (human fibroblasts from synovial membrane of OA patient).

Example 7

The Therapeutic Effect of Recombinant Human Galectin-8 Peptides on Collagen-Induced Arthritis (CIA) of DBA/1 Mice The therapeutic effect of recombinant human galectin-8 variants were analyzed on CIA induced mice (an animal model of human RA).

Materials and Methods

Animal treatment: 44 DBA/1 mice were induced with a joint inflammatory disease by two subcutaneous (s.c.) injections into the base of the tail of type II collagen three weeks apart. Joint inflammation, which appears several days after the last collagen injection, causes enhanced marked foot pad swelling, as well as swelling of other joints. The diameter of nonarthritic footpads is 1.5 to 1.7 mm. A footpad diameter of 1.9 to 2.0 mm was arbitrarily set as disease onset. Footpad thickness gradually increased, reaching a plateau at day 8. Human galectin-8 protein and variants (100 µg per injection) as well as control injections were injected IP at disease onset and then every day for 11 days.

The 44 mice were divided into 5 experimental groups as follows:

Group 1 (negative control): systemic injection (starting at CIA onset) of PBS or PBS+30% glycerol (storing dilution solution of galectin proteins) (10 mice).

Group 2 (positive control): systemic injection (starting at CIA onset) of anti-mouse TNFα mAb (cat. no. AMC-3012, Biosource Int. Inc. USA) adhering to the standard protocol (i.e., 100 µg antibody/mouse every day for 11 days) (6 mice).

Group 3 (positive control): systemic injection of human galectin-8 protein according to the standard protocol (10 mice).

Group 4: systemic injection of 100 µg per dose of human galectin-8 variant 1 according to the standard protocol (10 mice).

Group 5: systemic injection of 100 µg per dose of human galectin-8 variant 2 (8 mice).

The effect on footpad thickness was determined in a "blind" fashion, recording the electronic microcaliper measurements of the thickness of the joints, by picking the animals at random and recording their ears' signs following measurement. The mice were bled prior to disease induction, following disease onset and upon termination of the experiment (approximately day 11). The sera were stored and later analyzed for the presence of rheumatoid factor (RF) and cytokines. The mice were killed upon termination of the experiment and the joints removed from some of the animals for histopathological examination.

Histopathological examination: The rear footpad joints of 5 arthritic mice that received PBS or PBS+30% glycerol (group 1, negative control), 2 arthritic mice that received anti-mouse-TNFα mAb (group 2, positive control), 3 arthritic mice that received human galectin-8 protein (group 3, positive control), 3 normal healthy mice and 5 arthritic mice that received human galectin-8 variant 1 (group 4) were sent to an accredited pathological laboratory (Patho-Lab, Kiryat Weitzmann, Rehovot) for histopathological examination.

Quantification of the arthritic changes was made subjectively based on degree of articular destruction and following evaluation of the different parameters often observed in arthritic joints. The definition of the parameters quantitated were:

1. Cellularity within the joint: Cells present couldn't be identified due to loss of cellular morphology (decal), therefore red blood cells and leukocytes were all graded together.
2. Presence of fibrin in the joint: Fibrin was present in apparently more acute lesions, but the amount of fibrin was proportionally small.
3. Cartilage loss: Cartilage surfaces were evaluated in the section, slight changes of irregularity of the surface were noted.
4. Fibrosis: Fibrosis within the joint replacing bone and cartilage.
5. Synovial cell loss: Identification of synovial cells was difficult due to poor cellular morphology, but in general synovial surfaces were evaluated for integrity.
6. Periosteal apposition: Formation of new bone on periosteum.
7. Periarticular inflammation or hemorrhage: Presence of blood cells on the periphery of the joint area.
8. Periarticular fibrosis: Fibrosis surrounding the joint area.

The grade was based on the degree of articular destruction (fibrosis, inflammation, and necrosis of bone and cartilage) and does not represent an average of the histological parameters.

Results

Group 1 (negative control): PBS had no influence the course of CIA in the DBA/1 mice.

Group 2 (positive control): TNFα mAb markedly reduced CIA manifestations in DBA/1 mice (6 mice), as indicated by tracing footpad swelling.

Group 3 (positive control): systemic injection of human galectin-8 protein substantially reduced the CIA manifestations in the DBA/1 mice.

Group 4: systemic injection of 100 µg per dose of human galectin-8 variant 1 according to the standard protocol substantially reduced the CIA manifestations in the DBA/1 mice (10 mice).

Group 5: systemic injection of 100 µg per dose of human galectin-8 variant 2 according to the standard protocol did not influence the course of CIA in DBA/1 mice (8 mice).

The results are illustrated graphically in FIG. 14.

In conclusion, human galectin-8 variant 1 recombinant peptide was at least as effective as anti-TNFα mAb and the human galectin-8 recombinant peptide at alleviating the swelling in the footpad of CIA induced mice.

Histopathological Results

The pathological report is presented in Table 2 below.

TABLE 6

| ** | Articular cellularity | Fibrin | Cartilage loss | Fibrosis | Synovial cell loss | Periosteal apposition | Periarticular inflammation/ hemorrhage | Periarticular fibrosis | GRADE |
|---|---|---|---|---|---|---|---|---|---|
| 01 | 3 | 3 | 4 | 5 | 4 | 5 | 2 | 5 | 5 |
| 02 | 3 | 2 | 4 | 5 | 5 | 4 | 2 | 4 | 5 |
| 03 | 1 | 2 | 4 | 5 | 4 | 4 | 3 | 5 | 5 |
| 04 | 2 | 2 | 4 | 5 | 4 | 4 | 4 | 5 | 5 |
| 05 | 3 | 2 | 5 | 5 | 5 | 4 | 5 | 5 | 5 |
| 06 | 1 | 2 | 4 | 4 | 4 | 4 | 0 | 5 | 5 |
| 07 | 2 | 3 | 3 | 4 | 4 | 3 | 3 | 4 | 4 |
| 08 | 1 | 2 | 4 | 4 | 4 | 1 | 4 | 4 | 4 |
| 09 | 0 | 0 | 0 | 0 | 0 | 0 | 0 | 0 | 0 |
| 10 | 0 | 0 | 0 | 0 | 0 | 0 | 0 | 0 | 0 |
| 11 | 1 | 2 | 2 | 3 | 4 | 2 | 2 | 4 | 3 |
| 12 | 0 | 0 | 0 | 0 | 0 | 0 | 0 | 0 | 0 |
| 13 | 0 | 0 | 0 | 0 | 0 | 0 | 0 | 0 | 0 |
| 14 | 4 | 2 | 4 | 4 | 5 | 3 | 4 | 4 | 4 |
| 15 | 1 | 2 | 2 | 1 | 3 | 0 | 2 | 2 | 2 |
| 16 | 1 | 2 | 2 | 1 | 2 | 0 | 1 | 1 | 2 |
| 17 | 2 | 2 | 3 | 2 | 3 | 2 | 1 | 3 | 3 |
| 18 | 0 | 0 | 0 | 0 | 0 | 0 | 0 | 0 | 0 |
| 19 | 3 | 2 | 1 | 3 | 4 | 0 | 3 | 2 | 3 |
| 20 | 1 | 0 | 0 | 0 | 0 | 0 | 0 | 0 | 0 |
| 21 | 1 | 2 | 0.5 | 1 | 1 | 0 | 1 | 0 | 1 |
| 22 | 0 | 0 | 0 | 0 | 0 | 0 | 0 | 0 | 0 |
| 23 | 0 | 0 | 0 | 0 | 0 | 0 | 0 | 0 | 0 |
| 24 | 2 | 3 | 2 | 3 | 4 | 1 | 4 | 2 | 3 |
| 25 | 0 | 0 | 0 | 0 | 0 | 0 | 0 | 0 | 0 |
| 26 | 0 | 0 | 0 | 0 | 0 | 1 | 0 | 0 | 0 |
| 27 | 1 | 2 | 1 | 1 | 1 | 1 | 2 | 1 | 1 |
| 28 | 0 | 0 | 0 | 0 | 0 | 0 | 0 | 0 | 0 |
| 29 | 1 | 0 | 1 | 0 | 0 | 0 | 0 | 0 | 0 |
| 30 | 1 | 0 | 0.5 | 0 | 0 | 0 | 0 | 0 | 0 |
| 31 | 0 | 0 | 0 | 0 | 0 | 0 | 0 | 0 | 0 |
| 32 | 0 | 0 | 0 | 0 | 0 | 0 | 0 | 0 | 0 |
| 33 | 0 | 0 | 0 | 0 | 0 | 0 | 0 | 0 | 0 |
| 34 | 0 | 0 | 0 | 0 | 0 | 0 | 0 | 0 | 0 |
| 35 | 0 | 0 | 0 | 0 | 0 | 0 | 0 | 0 | 0 |
| 36 | 0 | 0 | 0 | 0 | 0 | 2* | 0 | 0 | 0 |

*there is metaphyseal periosteal deposition.
** In each couple of results described the first is right foot, the second is left foot.

The degree of articular destruction is illustrated graphically in FIG. 15.

Joints from arthritic mice treated with human galectin-8 variant 1 recovered, most of them completely and some at least partly, when compared with joints from arthritic mice treated with PBS or PBS+30% glycerol (negative control).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED

Additional References are Cited in the Text

1. Barondes S., Castronovo V., Cooper D., Cummings R. D., Drickamer K., Feizi T., Gitt M. A., Hirabayashi J., Hughes C., Kasai K., Leffler H., Liu F., Lotan R., Mercurio A., Monsigny M., Pillai S., Poirier F., Raz A., Rigby P., Rini J. M., Wang J. L., Galectins: a family of animal β-galactoside-binding lectins, Cell 76, 597-598, 1994a.
2. Cooper D. N., Barondes S. H., Evidence for export of a muscle lectin from cytosol to extracellular matrix and for a novel secretory mechanism, J. Cell Biol., 110 (5), 1681-1691, 1990.
3. Barondes S. H., Cooper D. N. W., Gitt M. A., Leffler H., Structure and function of a large family of animal lectins, J. Biol. Chem., 269 (33), 20807-20810, 1994b.
4. Wada J., Kanwar Y., Identification and characterization of galectin-9, a novel beta-galactoside-binding mammalian lectin, J. Biol. Chem., 272 (9), 6078-6086, 1997.
5. Drickamer K., Taylor M. E., Biology of animal lectins, Annu. Rev. Cell Biol., 110, 1681-1691, 1993.
6. Gitt M. A., Colnot C., Poirier F., Nani K. J., Barondes S. H., Leffler H., Galectin-4 and galectin-6 are two closely related lectins expressed in mouse gastrointestinal tract, J. Biol. Chem., 273 (5), 2954-2960, 1998.
7. Hadari Y., Paz K., Dekel K., Mestrovik T., Accili D., Zick Y., Galectin-8, a new rat lectin, related to galectin-4. Biol. Chem., 17, 3447-3453, 1995.

8. Mc Ever R. P., Moore K. L., Cummings R. D., Leucocyte trafficking mediated by selectin-carbohydrate interactions, J. Biol. Chem., 270, 11025-11028, 1995.
9. Schoeppner H. L., Raz A., Ho S. B., Bresalier R. S., Expression of an endogenous galactose-binding lectin correlates with neoplastic progression in the colon, Cancer 75, 2818-2826, 1995.
10. Yang R. Y., Hsu D. K., Liu F. T., Expression of galectin-3 modulates T-cell growth and apoptosis, Proc. Natl. Acad. Sci. USA 93, 6737-6742, 1996.
11. Bresalier R. S., Byrd J. C., Wang L., Raz A., Colon cancer mucin: a new ligand for the beta-galactoside-binding protein galectin-3, Cancer Res., 56, 4354-4357, 1996.
12. Cherayil B. J., Chaitovitz S., Wong C., Pillai S., Molecular cloning of human macrophage lectin specific for galactose, Proc. Natl. Acad. Sci. USA 87, 7324-7328, 1990.
13. Liu F. T., S-type mammalian lectins in allergic inflammation, Immunol. Today 14 (10), 486-490, 1993.
14. Jia S., Wang J. L., Carbohydrate binding protein 35: complementary DNA sequence reveals homology with proteins of the heterogeneous nuclear RNP, J. Biol. Chem., 263, 6009-6011, 1988.
15. Dagher S. F., Wang J. L., Patterson R. J., Identification of galectin-3 as a factor in pre-mRNA splicing, Proc. Natl. Acad. Sci. USA 92, 1213-1217, 1995.
16. Vyakarnam A., Dagher S., Wang J., Patterson D., Evidence for a role for galectin-1 in pre-mRNA splicing, Mol. Cell. Biol., 17, 4730-4737, 1997.
17. Leonidas D. D., Vatzaki E. H., Worum H., Celis J. E., Madsen P., Acharya K. R., Structural basis for the recognition of carbohydrates by human galectin-7, Biochemistry 37, 13930-13940, 1998.
18. Su Z., Lin J., Shen R., Fisher P., Goldstein N., Surface epitope masking and expression cloning identifies the human prostate carcinoma tumor antigen PCTA-1, a member of the galectin gene family, Proc. Natl. Acad. Sci. USA 93, 7252-7257, 1996.
19. Roehm N. W., Rodgers G. H., Hatfield S. M., Glasebrook A. L., An improved calorimetric assay for cell proliferation and viability utilizing the tetrazolium salt XTT, J. Immunol. Methods 142, 257-265, 1991.

What is claimed is:

1. A composition comprising the galectin-8 sequence set forth in SEQ ID NO: 6 or 8.

2. A composition comprising the galectin-8 sequence set forth in SEQ ID NO: 16.

3. A composition consisting of the galectin-8 sequence set forth in SEQ ID NO: 18.

* * * * *

UNITED STATES PATENT AND TRADEMARK OFFICE
CERTIFICATE OF CORRECTION

PATENT NO. : 8,076,087 B2  
APPLICATION NO. : 11/920054  
DATED : December 13, 2011  
INVENTOR(S) : Itshak Golan et al.

Page 1 of 1

It is certified that error appears in the above-identified patent and that said Letters Patent is hereby corrected as shown below:

Title Page:

Item (73), Assignees, line 2, change "Souraskv" to --Sourasky--.

Signed and Sealed this  
Twenty-eighth Day of February, 2012

David J. Kappos  
*Director of the United States Patent and Trademark Office*